(12) United States Patent
Yasukawa

(10) Patent No.: US 8,953,743 B2
(45) Date of Patent: Feb. 10, 2015

(54) X-RAY STRESS MEASUREMENT METHOD AND APPARATUS

(71) Applicant: Rigaku Corporation, Akishima-shi, Tokyo (JP)

(72) Inventor: Shoichi Yasukawa, Tokyo (JP)

(73) Assignee: Rigaku Corporation, Tokyo (JP)

( * ) Notice: Subject to any disclaimer, the term of this patent is extended or adjusted under 35 U.S.C. 154(b) by 110 days.

(21) Appl. No.: 13/917,829

(22) Filed: Jun. 14, 2013

(65) Prior Publication Data

US 2014/0029726 A1 Jan. 30, 2014

(30) Foreign Application Priority Data

Jul. 25, 2012 (JP) ................................. 2012-164632

(51) Int. Cl.
*G01N 23/20* (2006.01)
*G01L 1/25* (2006.01)
*G01N 23/207* (2006.01)

(52) U.S. Cl.
CPC ................ *G01L 1/25* (2013.01); *G01N 23/207* (2013.01)
USPC ........................................................ 378/72

(58) Field of Classification Search
CPC ................................ G01L 1/25; G01N 23/207
USPC .................................................... 378/70–72
See application file for complete search history.

(56) References Cited

FOREIGN PATENT DOCUMENTS

| JP | 7-77503 | A | 3/1995 |
|---|---|---|---|
| JP | 8-320264 | A | 12/1996 |
| JP | 11-64121 | A | 3/1999 |
| JP | 2000-213999 | A | 8/2000 |
| JP | 2004-93404 | A | 3/2004 |
| JP | 2004-132936 | A | 4/2004 |
| JP | 4039599 | B2 | 1/2008 |
| WO | 2012/015046 | A1 | 2/2012 |
| WO | 2012/015053 | A1 | 2/2012 |

OTHER PUBLICATIONS

He, Bob B., "Introduction to two-dimensional X-ray diffraction", Powder Diffraction, 2003, vol. 18, No. 2, pp. 71-85.
Nagai, Kin-chi et al., "Residual Stress on Fillet Weld Measured by X-ray Stress Analysis Using Informations of Debye-Scherrer Ring", Journal of the Japan Welding Society, 1977, vol. 46, No. 7, pp. 86-91.

*Primary Examiner* — Courtney Thomas
(74) *Attorney, Agent, or Firm* — Westerman, Hattori, Daniels & Adrian, LLP

(57) ABSTRACT

A sample (1) is irradiated with X-rays at different incident angles from plural X-ray sources (21, 22). Attention is focused on a Debye-ring of each X-ray diffraction emitted conically from the sample in association with incident X-ray from each of the X-ray sources (21, 22), and stress in the sample (1) is determined on the basis of information of X-ray diffraction appearing at an intersection point between the Debye-ring of the X-ray diffraction recorded on an image plate (30) and an equatorial plane (H) and information of X-ray diffraction appearing in the neighborhood of the intersection point between the Debye-ring and the equatorial plane (H).

12 Claims, 18 Drawing Sheets

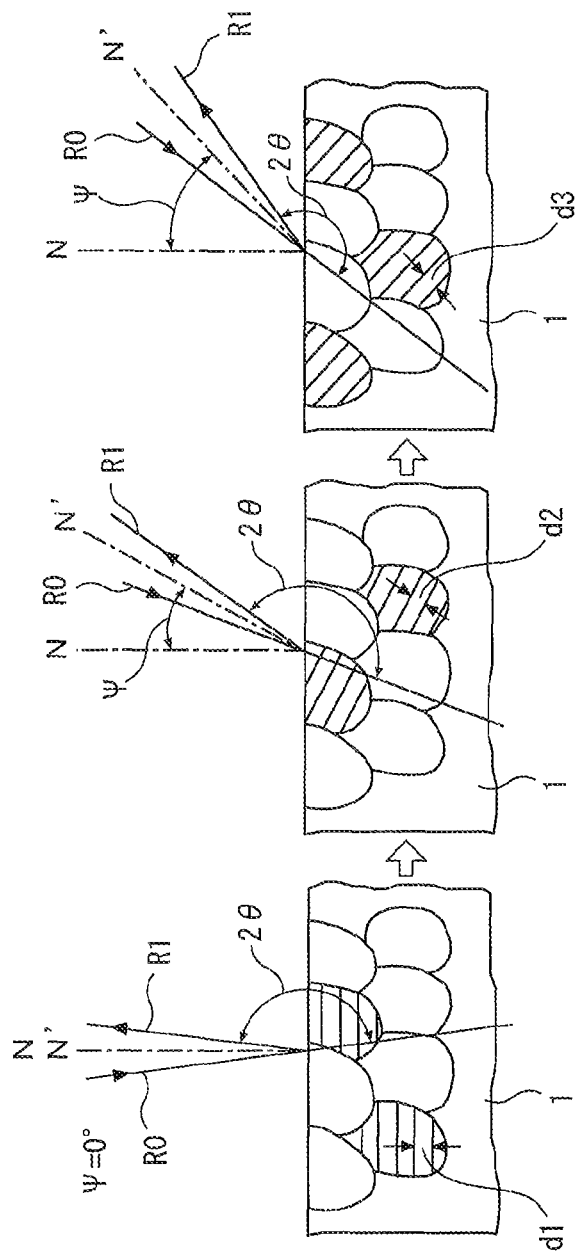

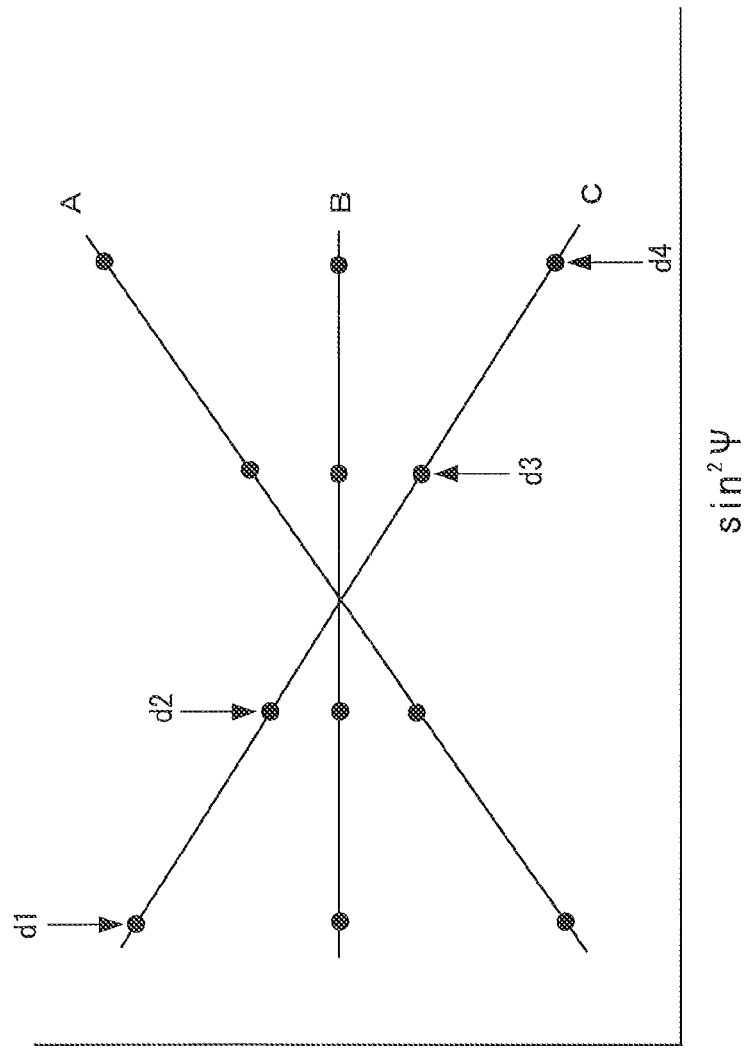

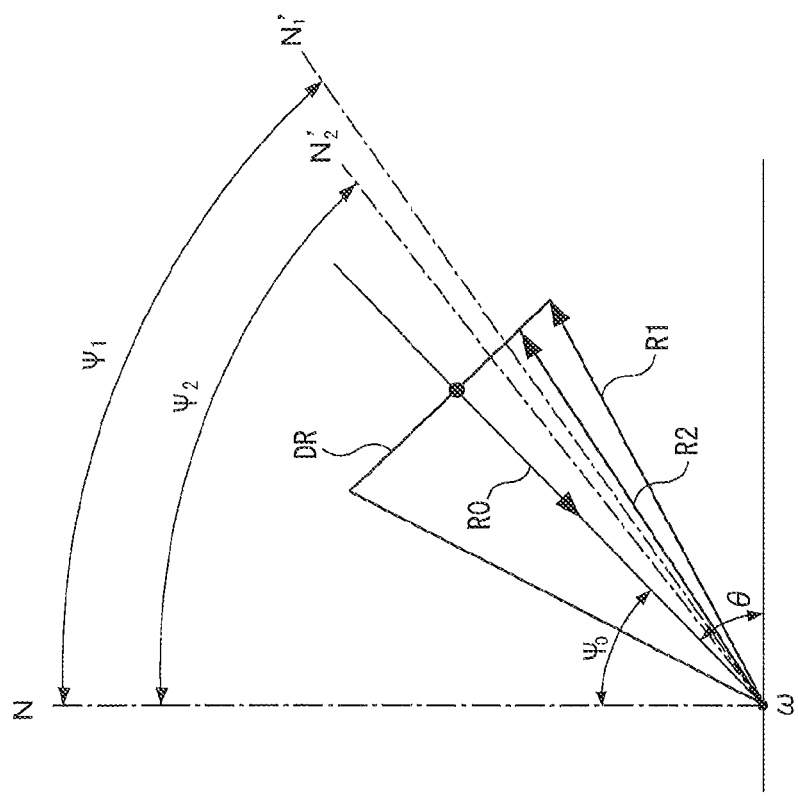
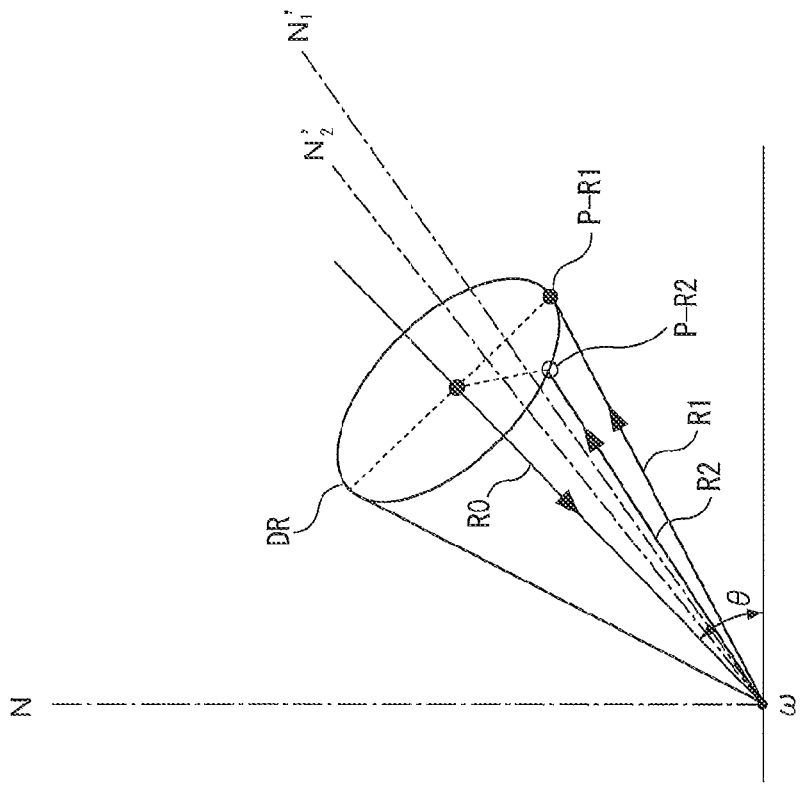

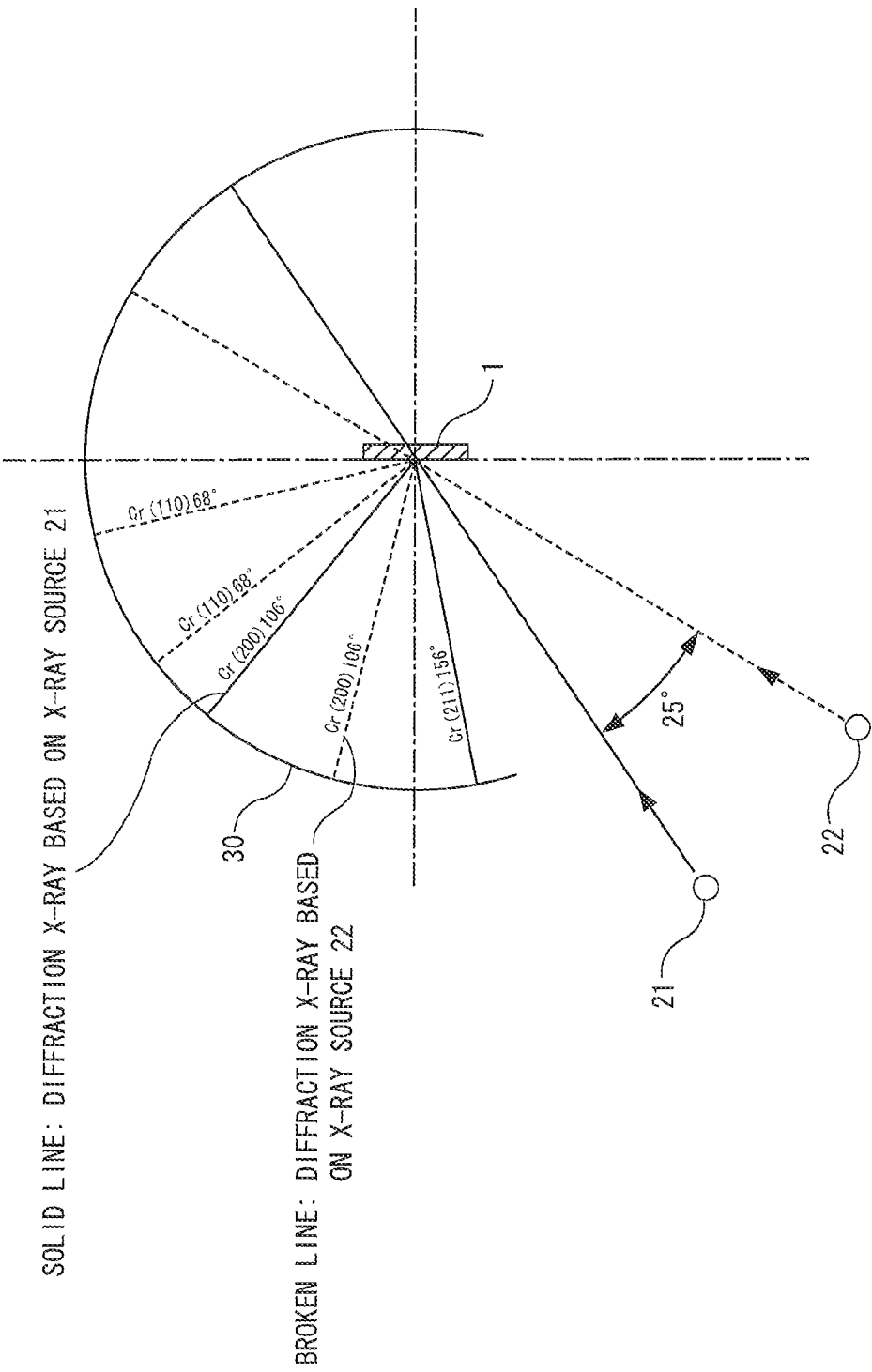

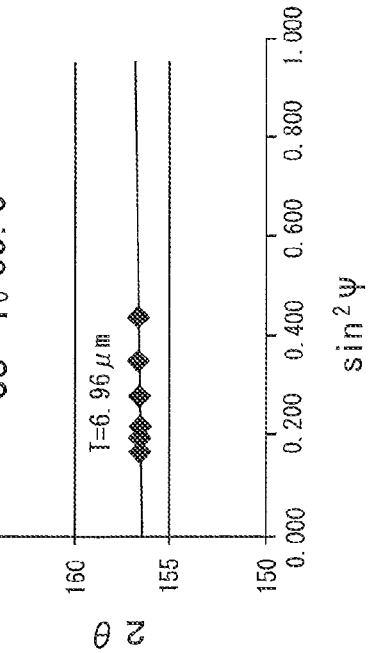
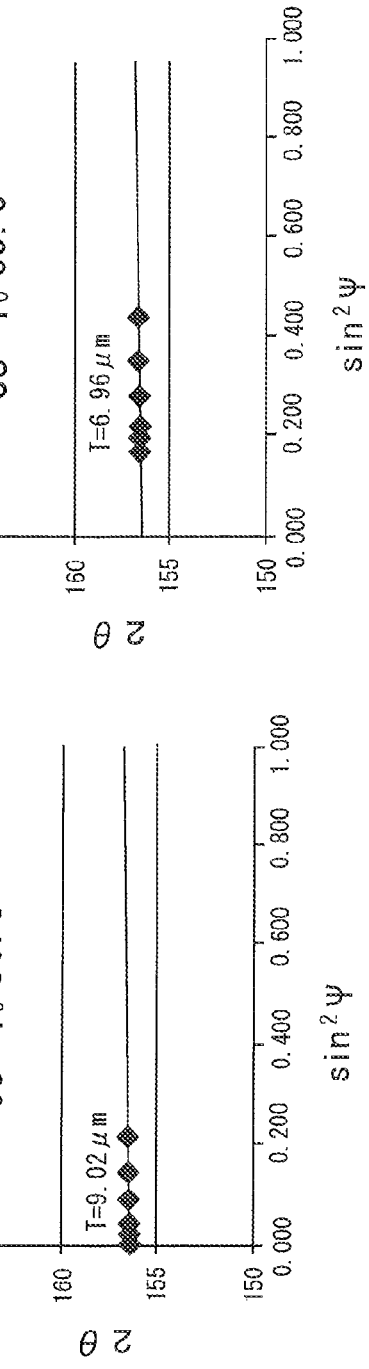
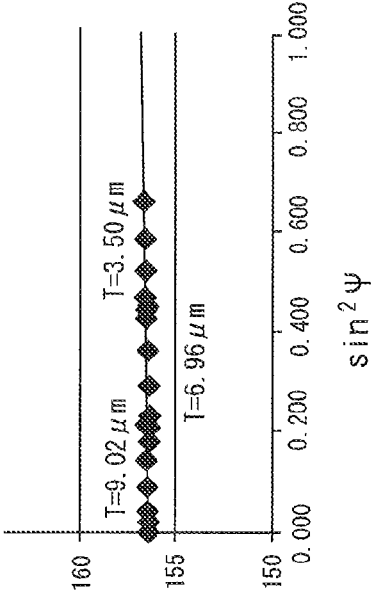
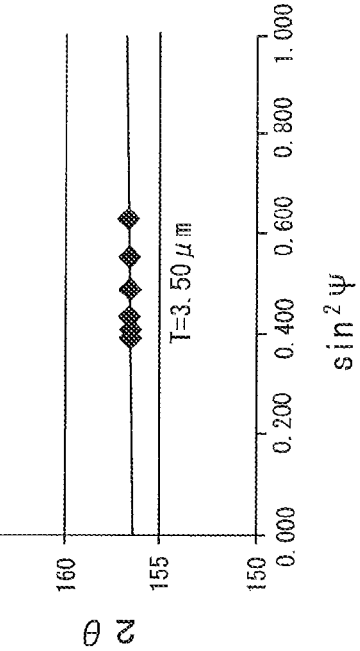

Co-Ψ₀ 65.0

Co-(200)

Co-Ψ₀ 36.8

Co-Ψ₀ 80.0

X-RAY STRESS MEASUREMENT METHOD AND APPARATUS

FIELD OF THE INVENTION

The present invention relates to X-ray stress measurement method and apparatus for measuring residual stress accumulated in a sample by using X-ray.

BACKGROUND OF THE INVENTION

An X-ray stress measurement method and an X-ray stress measurement apparatus have been broadly known, and the applicant of this application has already proposed plural inventions (see JP-A-08-320264, JP-A-2000-213999, JP-A-2004-93404 and WO2012/015046A1). The conventional X-ray stress measurement apparatus generally has one X-ray source mounted therein, and it is configured to irradiate a sample as a measurement target with X-ray from the X-ray source, detect X-ray diffraction from the sample and non-destructively measure stress of the sample on the basis of information of the X-ray diffraction. A method called as "$2\theta\text{-}\sin^2\Psi$ method" is known as such an X-ray stress measurement method as described above.

The $2\theta\text{-}\sin^2\Psi$ method will be briefly described hereunder.

In FIGS. 1A, 1B and 1C, a sample surface normal to a sample 1 is represented by N, and a lattice plane normal to internal crystal lattice planes of the sample 1 is represented by N'. The intersection angle $\Psi$ between the sample surface normal N and the lattice plane normal N' (generally called as "$\Psi$ angle") is varied from an angle state shown in FIG. 1A to an angle state shown in FIG. 1B and further varied to an angle state shown in FIG. 1C. At each $\Psi$ angle, X-ray R0 is incident to the sample 1, X-ray diffraction R1 diffracted from the crystal lattice planes is detected by an X-ray detector (not shown) and a diffraction angle $2\theta$ of each X-ray diffraction is determined.

Subsequently, the angle $\Psi$ used for the measurement is converted to "$\sin^2\Psi$", and the value of $\sin^2\Psi$ and the value of $2\theta$ measured every $\Psi$ angle are plotted on a graph, and these plotted points are subjected to straight-line approximation to obtain a "$2\theta\text{-}\sin^2\Psi$ line" as shown in FIG. 2. With respect to this $2\theta\text{-}\sin^2\Psi$ line, the gradient of the line is calculated by using the least-square method, and the calculated gradient is multiplied by a x-ray stress constant K, whereby a stress value as a measurement target is determined. The x-ray stress constant K is determined on the basis of the material properties (diffraction angle $2\theta$, Young's modulus and Poisson's ratio) of the sample and the wavelength of the X-ray used for the measurement.

In FIG. 2, a line A represents a state under which compression stress acts on the sample, and $d1>d2>d3>d4$ is satisfied. In FIG. 2, d1 to d4 represent lattice spacing. A line B represents a state under which free-stress acts on the sample, and $d1=d2=d3=d4$ is satisfied. A line C represents a state under which tensile stress acts on the sample, and $d1<d2<d3<d4$ is satisfied.

The $2\theta\text{-}\sin^2\Psi$ method described above has an advantage that the surface stress of the sample can be determined non-destructively with high accuracy. However, in order to determine the gradient according to the $2\theta\text{-}\sin^2\Psi$ method, it is required to vary the $\Psi$ angle at least two times and measure the position value of the diffraction angle $2\theta$ every time the $\Psi$ angle is varied, so that this method requires a long measurement time.

Furthermore, in order to determine the stress gradient in a depth direction of the sample by using the X-ray stress measurement apparatus having one X-ray source as described above, it is required to vary the incident angle of the X-ray to the sample or repetitively perform the stress measurement while plural kinds of X-ray sources having different wavelengths are exchanged by one another. Therefore, this method has a problem that the measurement time is further longer.

SUMMARY OF THE INVENTION

The present invention has been implemented in view of the foregoing circumstances, and has an object to speed up a measurement of stress acting on a sample by simultaneously obtaining information of difference X-rays at plural $\Psi$ angles.

Furthermore, the present invention has another object to further speed up a measurement of the stress gradient in a depth direction of the sample.

In order to attain the above objects, according to a first aspect of the present invention, an X-ray stress measurement method comprises: irradiating a sample with X-rays at a plurality of different incident angles from a plurality of X-ray sources; focusing attention on a Debye-ring of each X-ray diffraction radiated conically from the sample in association with incident X-ray emitted from each of the X-ray sources; and determining stress in the sample on the basis of information of X-ray diffraction appearing at an intersection point between the Debye-ring and an equatorial plane containing the optical axis of the incident X-ray emitted from each of the X-ray sources, and information of X-ray diffraction appearing at a point on the Debye-ring that is other than the intersection point between the Debye-ring and the equatorial plane, more preferably information of X-ray diffraction appearing in the neighborhood of the intersection point.

As described above, according to the X-ray stress measurement method of the first aspect of the present invention, the X-ray is incident from the plural X-ray sources to the sample at the plural different incident angles. Therefore, each incident X-ray to the sample is diffracted from plural crystal lattice planes in the sample, and X-ray diffractions at plural $\Psi$ angles appear. Accordingly, the information of the X-ray diffractions associated with the plural $\Psi$ angles can be simultaneously obtained, and the measurement can be rapidly performed.

Furthermore, the X-ray stress measurement method according to the first aspect of the present invention uses the information of the X-ray diffraction appearing at the intersection point between the Debye-ring of each X-ray diffraction radiated from the sample and the equatorial plane, and the information of the X-ray diffraction appearing at a point on the Debye-ring that is other than the intersection point between the Debye-ring and the equatorial plane, more preferably the information of the X-ray diffraction appearing in the neighborhood of the intersection point, so that the information of the X-ray diffractions associated with a larger number of different $\Psi$ angles can be simultaneously obtained.

This feature will be described in more detail with reference to FIGS. 3A and 3B.

FIGS. 3A and 3B are diagrams showing the relationship between X-ray diffraction on a Debye-ring and $\Psi$ angle, wherein FIG. 3A is a view taken from an obliquely upper side and FIG. 3B is a diagram obtained by projecting the X-ray diffraction onto an equatorial plane.

As shown in FIG. 3A, when a sample is irradiated with X-ray R0, the X-ray is diffracted at a crystal lattice in the sample, and X-ray diffraction circumferentially radiates conically around the optical axis of the incident X-ray R0. A circular outer edge line DR of the bottom surface of a cone corresponding to the locus of the radiated X-ray diffraction is called as a Debye-ring. For example when the conically radiating X-ray diffraction is received by a flat-plate type image plate, a diffraction pattern based on Debye-rings DR which are concentric with one another around the incident X-ray are obtained on the image plate.

Furthermore, when X-ray stress measurement is performed, a sample and an X-ray source are relatively rotated around an ω axis passing the surface of the sample to vary the incident angle $\Psi_0$ of X-ray to the sample. The $\Psi$ angle shown in FIGS. 1A, 1B, 1C is adjusted by varying the incident angle $\Psi_0$. Here, a virtual flat plane which contains the optical axis of the X-ray (incident X-ray) emitted from the X-ray source and is perpendicular to the ω axis is called as "equatorial plane". In this invention, plural X-ray sources are arranged along the equatorial plane and set so that the optical axes of X-rays (incident X-rays) emitted from the respective X-ray sources travel (extend) on the same equatorial plane.

The stress of the sample is normally analyzed by using information of X-ray diffraction R1 appearing at a intersection point P-R1 between a Debye-ring DR based on X-ray diffraction R1 and the equatorial plane (information recorded on the image plate). As shown in FIG. 3B, the intersection angle $\Psi_1$ between the lattice plane normal $N_1'$ associated with the X-ray diffraction R1 and the sample surface normal N on the equatorial plane is the $\Psi$ angle in the $2\theta\text{-sin}^2 \Psi$ method (see FIG. 1A, FIG. 1B, FIG. 1C).

Subsequently, as shown in FIG. 3A, attention is focused on X-ray diffraction R2 appearing at a point P-R2 on the Debye-ring DR which is a point other than the intersection point between the equatorial plane and the Debye-ring DR. The lattice plane normal $N_2'$ associated with the X-ray diffraction R2 is displaced from the lattice plane normal $N_1'$. As shown in FIG. 3B, the lattice plane normal $N_2'$ is projected onto the equatorial plane, and an intersection angle $\Psi_2$ between the lattice plane normal $N_2'$ and the sample surface normal N is determined. The angle $\Psi_2$ is different from the angle $\Psi_1$ described above. Accordingly, the information of the X-ray diffraction R2 appearing at the point P-R2 on the Debye-ring which is a point other than the intersection point between the Debye-ring and the equatorial plane (the information recorded on the image plate) and the angle $\Psi_2$ can be used as information associated with a different $\Psi$ angle to analyze the stress based on the $2\theta\text{-sin}^2 \Psi$ method, for example.

Information of X-ray diffraction at one $\Psi$ angle has been hitherto obtained every time the incident angle of X-ray to the sample is set. However, according to the method of the first aspect of the present invention, information of X-ray diffraction associated with plural $\Psi$ angles can be obtained every one X-ray incident angle is set. In addition, since X-ray is incident at plural different incident angles from plural X-ray sources, information of X-ray diffraction associated with plural $\Psi$ angles can be obtained every incident X-ray. Accordingly, the measurement frequency (frequency of scanning) required to obtain information necessary for the analysis of stress can be remarkably reduced, and the rapid measurement can be performed.

According to a second aspect of the present invention, as an apparatus suitable to perform the X-ray stress measurement method according to the first aspect of the present invention, an X-ray stress measurement apparatus comprises: a sample table on which a sample is mounted; a plurality of X-ray sources that irradiate the sample with X-rays; an X-ray detector that detects X-ray diffractions diffracted from crystal lattice planes in the sample; an apparatus main body in which the sample table, the X-ray sources and the X-ray detector are mounted; and an analyzer that determines stress in the sample on the basis of information of the X-ray diffraction detected by the X-ray detector, wherein the plurality of X-ray sources are arranged so as to make X-rays incident to a desired incident point set on a surface of the sample at different incident angles, the X-ray detector has a function capable of collectively detecting plural X-ray diffractions emitted from the sample, and the analyzer focuses attention to a Debye-ring of X-ray diffraction radiated conically from the sample in association with incident X-ray emitted from each of the X-ray sources, and determines stress in the sample on the basis of information of X-ray diffraction appearing at a intersection point between the Debye-ring and an equatorial plane containing the optical axis of the incident X-ray emitted from each of the X-ray sources, and information of X-ray diffraction appearing at a point on the Debye-ring that is other than the intersection point between the Debye-ring and the equatorial plane (preferably information of X-ray diffraction appearing in the neighborhood of the intersection point).

Furthermore, in the X-ray stress measurement method according to the first aspect of the present invention, X-rays having different wavelengths may be emitted from the plurality of X-ray sources to determine a stress gradient in a depth direction of the sample.

That is, the arrival depth of the incident X-ray to the inside of the sample varies according to the incident angle and wavelength of the X-ray and the sample. Therefore, with respect to each of X-rays emitted from the plural X-ray sources, the arrival depth of the incident X-ray to the inside of the sample is adjusted by setting the incident angle and specifying the wavelength, and information of X-ray diffractions from different depths is obtained in a lump (simultaneously), whereby the measurement frequency (frequency of scanning) required to obtain information necessary for determining the stress gradient in the depth direction of the sample can be remarkably reduced, and the rapid measurement can be performed.

In the X-ray stress measurement apparatus according to the second aspect of the present invention, as the apparatus suitable to perform the above method, it is preferable that the plural X-ray sources are configured to emit X-rays having different wavelengths, and the analyzer has a function of determining the stress gradient in the depth direction of the sample.

Furthermore, the X-ray stress measurement method according to the first aspect of the present invention may use steel material as the sample, and determine a distribution of retained austenite in the depth direction of the sample.

Steel is formed of texture called as ferrite (α-Fe) at room temperature. However, when ferrite is heated to high temperature, it changes to austenite (Y-Fe). When the thus-obtained austenite is rapidly cooled (quenched), rigid and fragile texture called as martensite is generated. At this time, a part of austenite does not change, but remains as austenite. This austenite is called as retained austenite. The texture portion of retained austenite is unstable and low in hardness at room temperature, which is liable to cause damage. Therefore, it is important to grasp the distribution condition of retained austenite for parts, structures, etc. formed of steel.

According to the X-ray stress measurement method of the first aspect of the present invention, X-rays having different wavelengths are incident to a sample at different angles from plural X-ray sources, whereby information of X-ray diffractions from different depths of the sample can be collectively obtained. Therefore, the measurement frequency (frequency of scanning) required to obtain information necessary for determining the distribution condition of retained austenite in the depth direction of the sample can be remarkably reduced, and rapid measurement can be performed.

As the apparatus suitable to perform the above method, the X-ray stress measurement apparatus according to the second aspect of the present invention is preferably configured so that steel material is used as the sample and the analyzer has a function of determining the distribution of retained austenite in the depth direction of the sample.

Furthermore, in the X-ray stress measurement method according to the first aspect of the present invention, the relative intersection angle between the optical axes of X-rays emitted from the plural X-ray sources may be changed to determine the stress of the sample.

As described above, the directions of X-ray diffractions radiated from the sample are properly adjusted by suitably changing the relative intersection angle between the optical axes of the X-rays emitted from the plural X-ray sources, whereby the information of the X-ray diffractions can be effectively obtained with no waste while the X-ray diffractions are avoided from being overlapped with one another.

As the apparatus suitable to perform the above method, the x-ray stress measurement apparatus according to the second aspect of the present invention is preferably provided with an angle adjusting unit that changes the relative intersection angle between the optical axes of the X-rays emitted from the plural X-ray sources.

In the X-ray stress measurement method according to the first aspect of the present invention, it is preferable to determine the stress of the sample surface, typically according to the foregoing $2\theta$-$\sin^2\Psi$ method. In this case, the incident angles of the X-rays applied to the sample from the plural X-ray sources are changed as occasion demands, whereby information of X-ray diffractions associated with a larger number of $\Psi$ angles can be obtained and thus the measurement precision can be enhanced.

It is needless to say that the X-ray stress measurement method according to the first aspect of the present invention may determine the stress of the sample by an analyzing method other than the $2\theta$-$\sin^2\Psi$ method.

As the apparatus suitable to perform the above method, the X-ray stress measurement apparatus according to the second aspect of the present invention is preferably configured so that the plural X-ray sources are arranged in the apparatus main body, and an incident angle changing mechanism for rotating the sample table around the axis passing the incident point to be perpendicular to the equatorial plane is provided to change the incident angles of the respective X-rays emitted from the plural X-ray sources to the sample, and the analyzer has a function of determining the stress of the sample surface according to the $2\theta$-$\sin^2\Psi$ method.

Furthermore, in the X-ray stress measurement apparatus according to the second aspect of the present invention, it is preferable that the X-ray detector comprises an image plate and is arranged arcuately around the sample so as to be capable of capturing X-ray diffractions radiated from the sample.

The image plate has no wavelength-dependence on detectable X-ray. Accordingly, when the image plate is disposed arcuately around the sample, X-ray diffractions radiated in various directions from the sample can be detected in a lump, and thus the image plate is an important constituent element for performing rapid measurement.

As described above, according to the present invention, information of X-ray diffractions associated with plural $\Psi$ angles can be simultaneously obtained, and thus speed-up of the stress measurement can be implemented.

Furthermore, according to the present invention, the rapid measurement can be performed on the stress gradient in the depth direction of the sample and the distribution of retained austenite in the depth direction of the sample.

BRIEF DESCRIPTION OF THE DRAWINGS

FIGS. 1A, 1B and 1C are diagrams showing a measurement method of stress based on the $2\theta$-$\sin^2\Psi$ method;

FIG. 2 is a diagram showing $2\theta$-$\sin^2\Psi$ lines used for the stress measurement based on the $2\theta$-$\sin^2\Psi$ method;

FIGS. 3A and 3B are diagrams showing the relationship between X-ray diffraction on a Debye-ring and $\Psi$ angle, wherein FIG. 3A is the diagram viewed from an obliquely upper side and FIG. 3B is the diagram obtained by projecting X-ray diffraction on an equatorial plane;

FIG. 6 is a diagram showing an example for stress measurement of a sample based on the X-ray stress measurement method according to the present invention;

FIGS. 16A to 16D are diagrams showing $2\theta$-$\sin^2\Psi$ lines determined on the basis of information of X-ray diffracted from $\alpha$-Fe (211) plane in association with incident X-ray of Co—K$\alpha$;

DETAILED DESCRIPTION OF THE EMBODIMENT

An embodiment according to the present invention will be described hereunder with reference to the drawings.

[Construction of X-ray Stress Measurement Apparatus]

First, an X-ray stress measurement apparatus according to an embodiment of the present invention will be described with respect to FIGS. 4, 5A and 5B.

Figure 4:
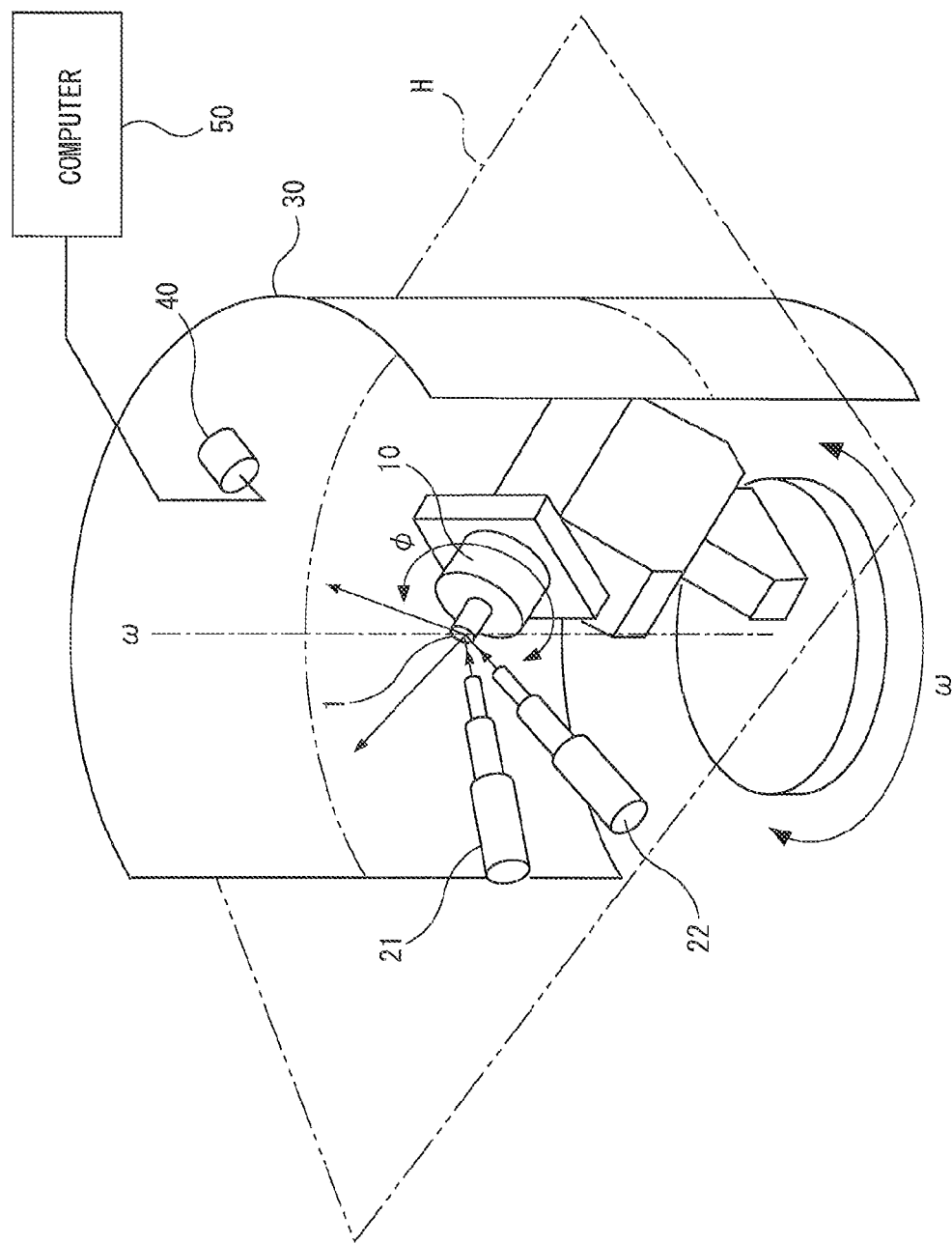
FIG. 4 is a perspective view showing an X-ray stress measurement apparatus according to an embodiment of the present invention.
Figure 5A:
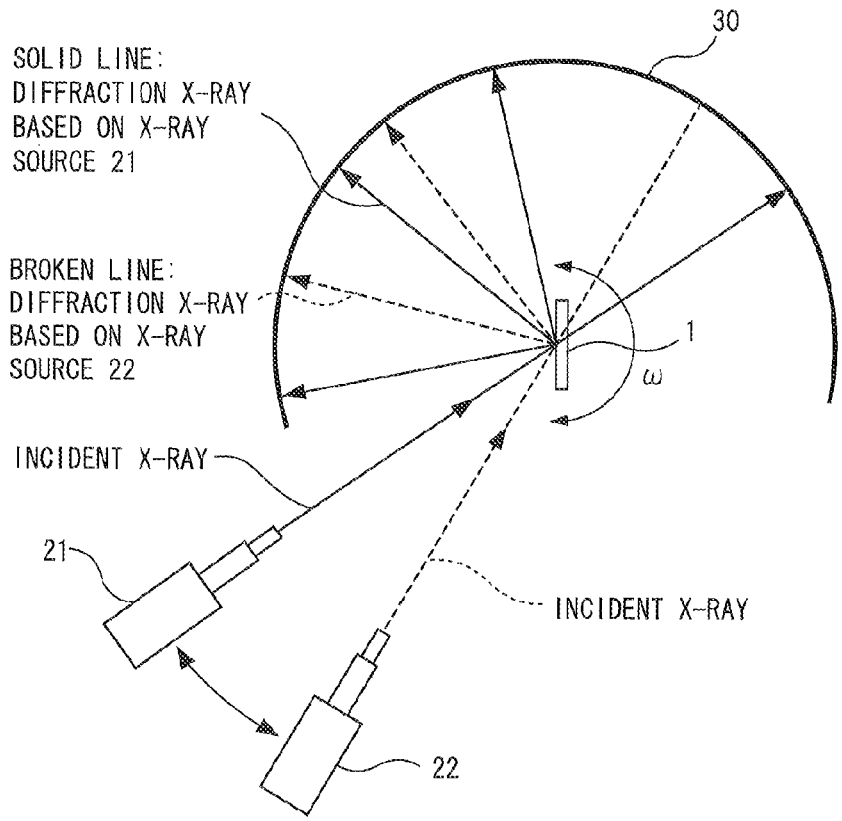
FIG. 5A is a plan view of the apparatus shown in FIG. 4.

FIG. 4 is a perspective view showing the X-ray stress measurement apparatus according to the embodiment. FIG. 5A is a plan view showing the apparatus shown in FIG. 4, and FIG. 5B is a front view showing an image plate which is used for the apparatus and planarly developed.

As shown in FIG. 4, the X-ray stress measurement apparatus has a sample table 10 for holding a sample 1 while the sample 1 is disposed at the tip of the sample table 10, two X-ray sources 21 and 22 for irradiating the surface of the sample 1 with X-ray, an image plate 30 (X-ray detector) for detecting and recording X-ray diffraction diffracted from crystal lattice planes in the sample 1, a reading device 40 for reading X-ray diffraction information recorded on the image plate 30, and a computer 50 (analyzer) for performing data analysis on the basis of the X-ray diffraction information read by the reading device 40 to determine stress in the sample 1, a stress gradient in the depth direction of the sample 1, a distribution in the depth direction of retained austenite, etc.

In this embodiment, the two X-ray sources 21 and 22 as heavy loads are mounted on the main body (not shown) of the apparatus. The apparatus is configured so that the sample table 10 is rotated around an $\omega$-axis passing the surface of the sample 1 to change the incident angle of X-ray which is emitted from each of the X-ray sources 21 and 22 and applied to the surface of the sample 1. That is, a mechanism of rotating the sample table 10 around the $\omega$-axis is configured as an incident angle changing mechanism for changing the incident angle of the X-ray to the surface of the sample 1.

Here, the optical axis of the X-ray (incident X-ray) emitted from each of the X-ray sources 21 and 22 is adjusted so as to intersect with the $\omega$-axis on the surface of the sample 1. This intersection point is set as an incidence point of X-ray on the surface of the sample 1. The incident points on the sample surface of respective X-rays emitted from the X-ray sources 21 and 22 are the same point.

The respective X-ray sources 21 and 22 are arranged so that the optical axes of X-rays emitted from the respective X-ray sources 21 and 22 travel (extend) on a virtual flat plane H which passes an incident point of X-ray on the surface of the sample and is perpendicular to the $\omega$-axis. Accordingly, the virtual flat plane H corresponds to an equatorial plane.

The installation positions of the respective X-ray sources 21 and 22 are adjusted so that the X-rays emitted from the X-ray sources 21 and 22 are incident to an incident point on the sample surface at different incident angles. Furthermore, the X-ray sources 21 and 22 may be selectively mounted so as to emit X-rays having the same wavelength or X-rays having different wavelengths in accordance with a measurement content.

In addition, an angle adjusting mechanism for changing the relative intersection angle at which the optical axes of the X-rays emitted from the X-ray sources 21 and 22 intersect with each other is installed in one of the two X-ray sources 21 and 22. Accordingly, the relative intersection angle between the optical axes of the X-rays emitted from the X-ray sources 21 and 22 is properly changed by the angle adjustment mechanism to thereby properly adjust the direction of X-ray diffraction emitted from the sample 1, so that superposition of X-ray diffractions recorded on the image plate 30 can be avoided and X-ray diffraction information can be effectively obtained without any waste.

The image plate 30 as the X-ray detector has no wavelength-dependency and can detect X-rays having various wavelengths. In addition, it has a function of detecting and recording, in a lump, X-ray diffractions appearing from the sample 1 at various angles. According to this embodiment, the flat type image plate 30 is disposed to be arcuately curved around the sample 1 so that it can capture X-ray diffractions emitted from the sample 1 disposed on the sample table 10. The intersection line between the thus-disposed image plate 30 and the equatorial plane H described above is defined as an equatorial line.

Figure 5B:
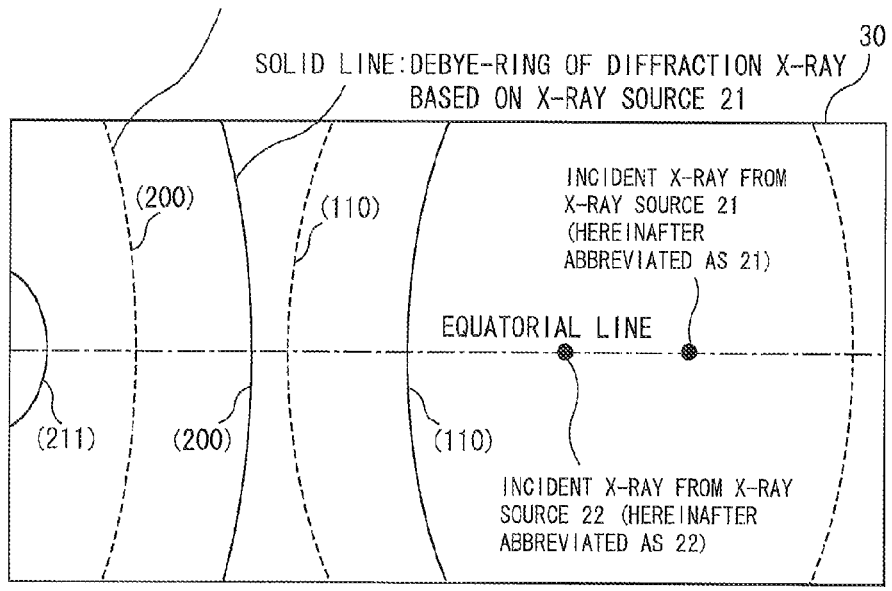
FIG. 5B is a front view when an image plate used for the apparatus is developed planarly.

As shown in FIG. 5B, information of X-ray diffractions diffracted from plural lattice planes (lattice planes of (211), (200) and (110) in the example of FIG. 5B) in the sample 1 is recorded on the image plate 30. Each X-ray diffraction is recorded in an arcuate shape as a part of a Debye-ring as described above.

The reading device 40 for the image plate 30 is publicly known, and the detailed description thereof is omitted. The computer 50 as an analyzer has a function of analyzing stress in the sample 1, a stress gradient in the depth direction of the sample 1, a distribution in the depth direction of retained austenite, etc. (analysis contents) on the basis of the information of the X-ray diffractions read from the image plate 30 according to a measurement method described later. The analysis of these analysis contents is performed on the basis of analysis programs pre-recorded in the computer 50.

The reading device 40 and the computer 50 are configured as units which are installed separately from the main body of the apparatus in which the sample table 10, the X-ray sources 21 and 22 and the image plate 30 are mounted. The image plate 30 is detached from the main body of the apparatus after the measurement is finished, and scanned to read the X-ray diffraction information by the reading device 40 as a separate unit.

[Example of Stress Measurement]

Next, an example of a stress measurement of a sample based on the X-ray stress measurement method according to the present invention will be described with reference to FIGS. 6 to 10.

In this example, the stress of the sample 1 is determined according to the $2\theta$-$\sin^2 \Psi$ method described above by using the two X-ray sources 21 and 22 for emitting X-rays having the same wavelength. Specifically, $\alpha$-Fe is used as a sample 1, two X-ray sources 21 and 22 for emitting X-rays of K$\alpha$ (Cr—K$\alpha$) emitted from Cr targets are arranged at an offset angle of 25° (that is, the X-ray sources are arranged at an angular interval of 25°) as shown in FIG. 6, and the sample 1 is irradiated with X-rays at different incident angles from the X-ray sources 21 and 22, respectively.

Figure 7:
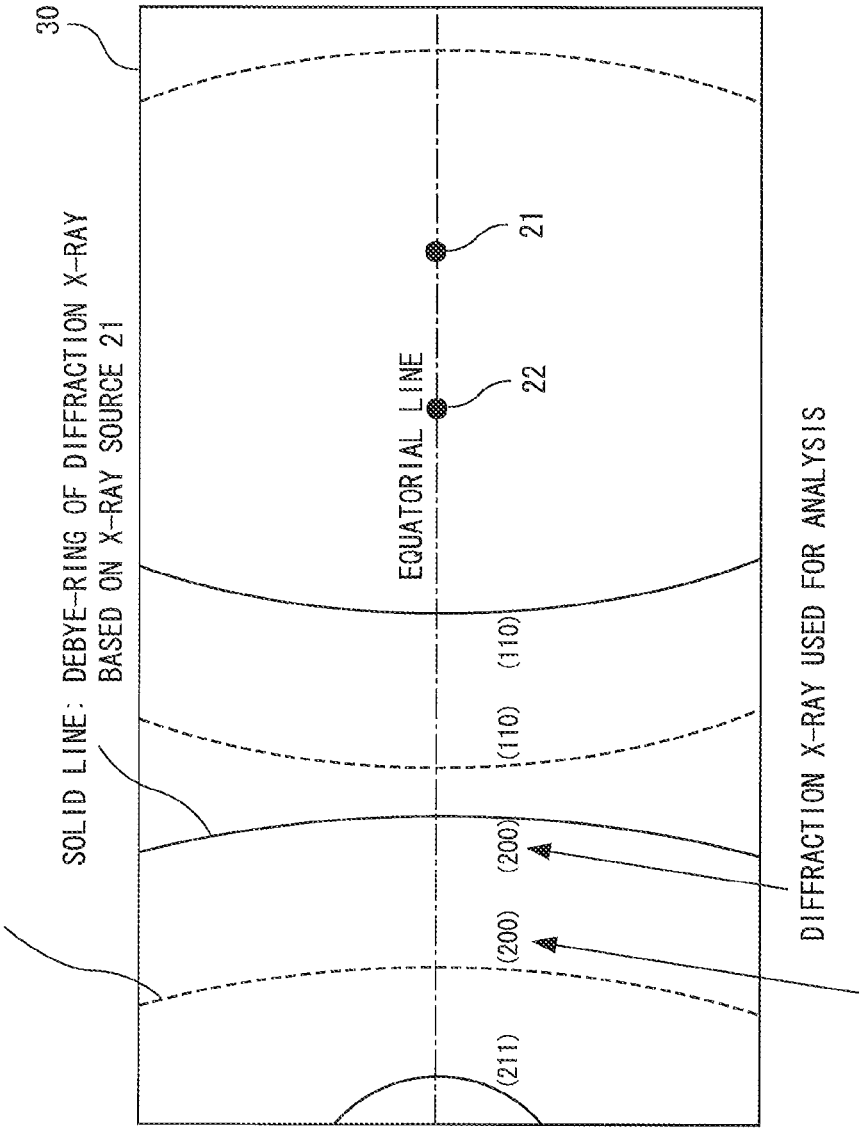
FIG. 7 is a diagram showing information of X-ray diffraction recorded on an image plate in the stress measurement of the sample based on the X-ray stress measurement method according to the present invention.

In general, information of X-ray diffractions diffracted from (200) and (211) lattice planes is used for the measurement of the stress of $\alpha$-Fe. When $\alpha$-Fe is irradiated with X-ray of Cr—K$\alpha$, under the condition that $\alpha$-Fe has no in-plane anisotropy, X-ray diffraction appears in the direction of the diffraction angle $2\theta \approx 106°$ with respect to the lattice planes of (200). Furthermore, X-ray diffraction appears in the direction of the diffraction angle $2\theta \approx 156°$ with respect to the lattice planes of (211). In this example, as shown in FIG. 7, the stress of the sample 1 is determined according to the $2\theta$-$\sin^2 \Psi$ method by using the information of the X-ray diffraction diffracted from the lattice planes of (200).

The incident angles of the X-rays emitted from the X-ray sources 21 and 22 to the sample 1 are adjusted so that the X-ray diffractions from the (200) lattice planes are recorded on the image plate 30. The incident angles of the X-rays emitted from the X-ray sources 21 and 22 to the sample 1 are different from each other by an offset angle of 25°. Therefore, the information of the X-ray diffractions diffracted from the (200) lattice planes with respect to the incident X-rays emitted from the X-ray sources 21 and 22 contains the information of two different X-ray diffractions between which the $\Psi$ angle in the $2\theta$-$\sin^2 \Psi$ method is different by 25°. Here, the $\Psi$ angle can be calculated from the incident angle of the X-ray emitted from each of the X-ray sources 21 and 22 to the sample 1.

Figure 8:
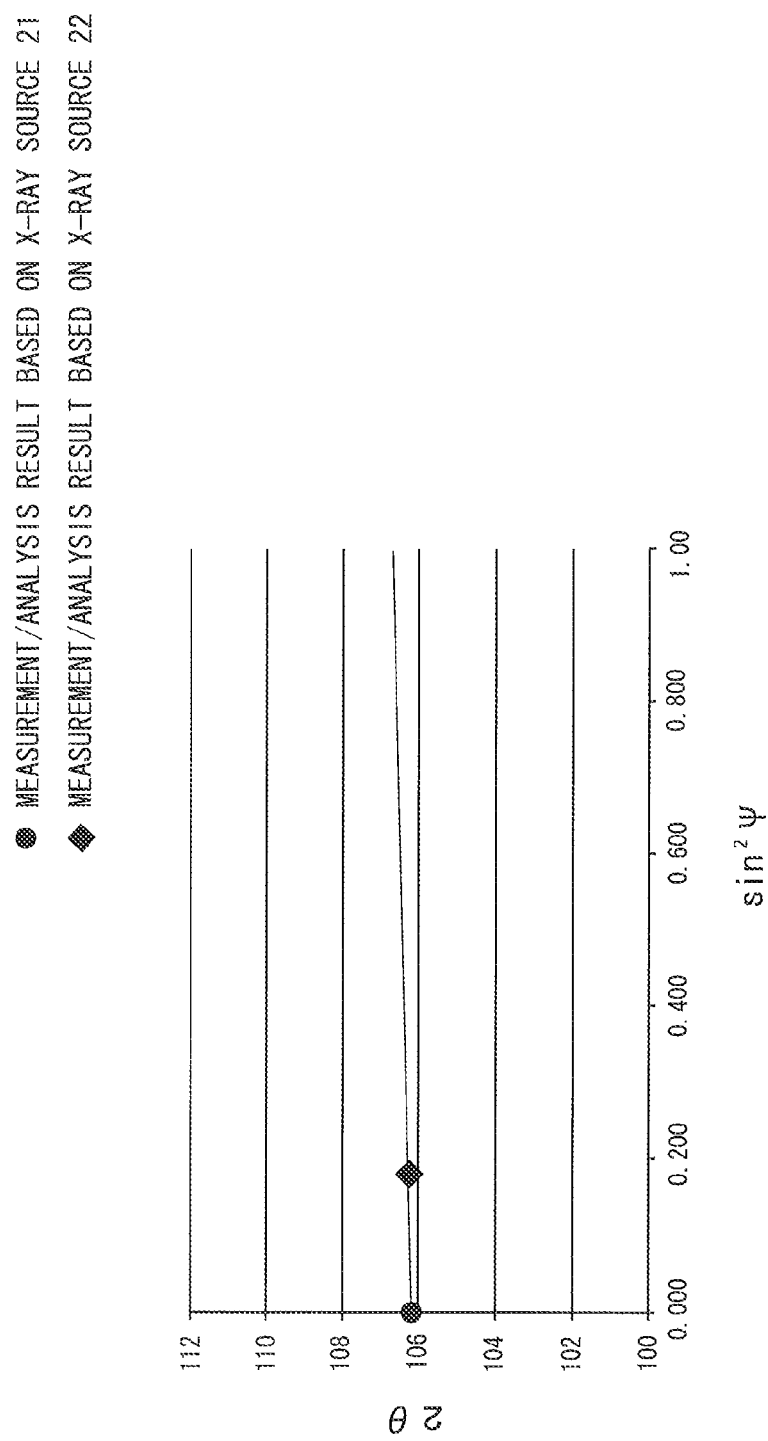
FIG. 8 is a diagram showing a $2\theta$-$\sin^2\Psi$ line created on the basis of the information of the X-ray diffraction shown in FIG. 7.
Figure 9:
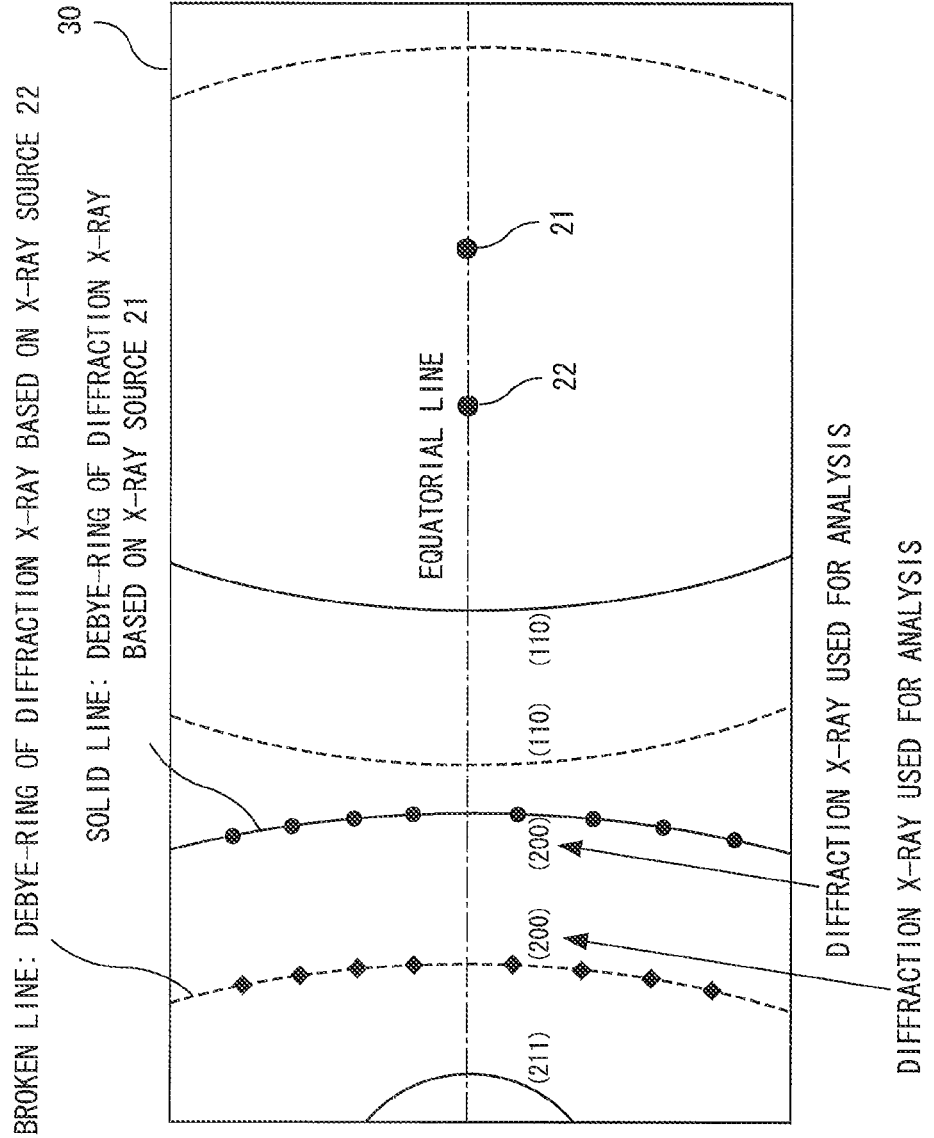
FIG. 9 is a diagram showing information of X-ray diffractions at plural points which appear in the neighborhood of intersection points between a Debye-ring of X-ray diffraction and an equatorial line.

With respect to the X-ray diffractions associated with the two $\Psi$ angles, attention is first focused to information of X-ray diffractions on the equatorial line, and the diffraction angle $2\theta$ determined from the X-ray diffraction recorded on the image plate 30 and the $\sin^2 \Psi$ value to which the $\Psi$ angle is converted are plotted on a $2\theta$-$\sin^2 \Psi$ diagram as shown in FIG. 8.

Figure 10:
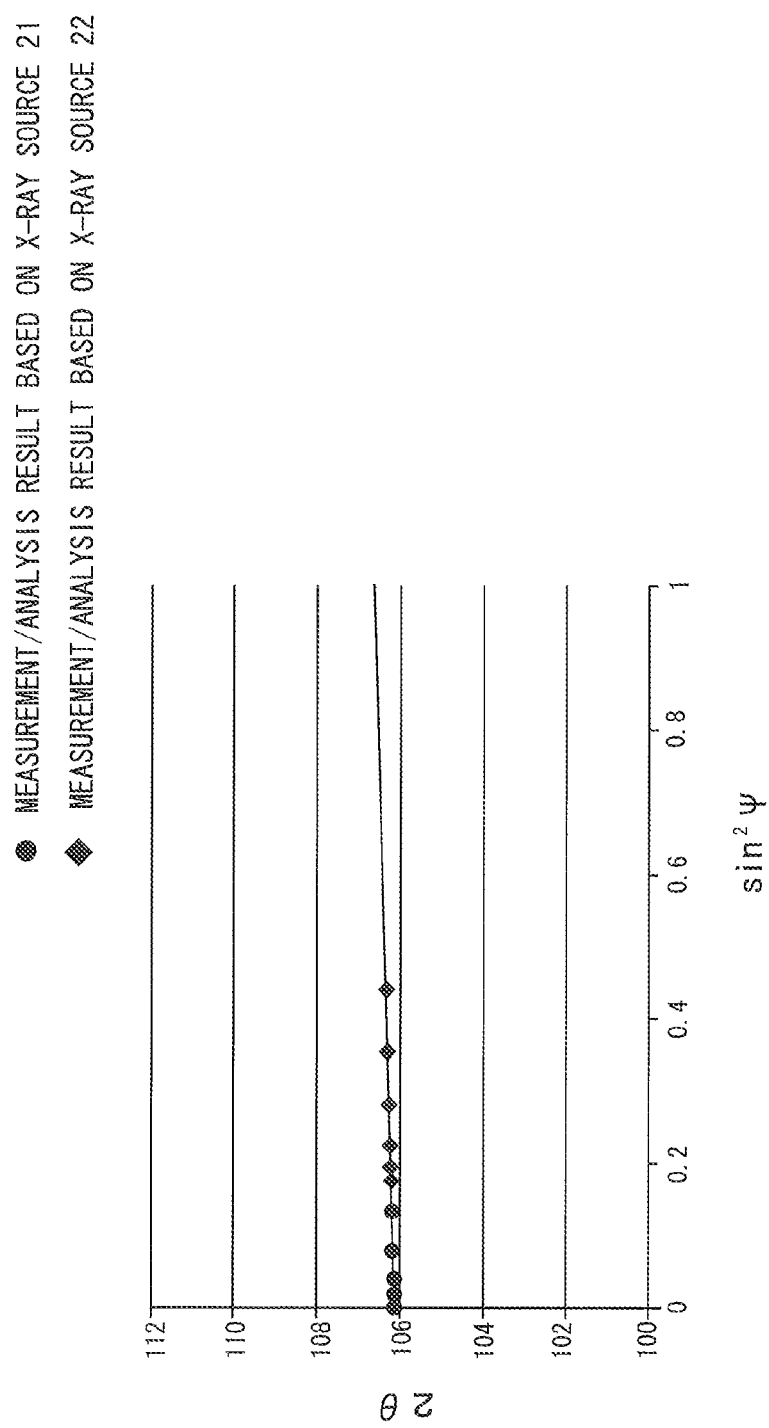
FIG. 10 is a diagram showing the $2\theta$-$\sin^2\Psi$ line based on the information of the X-ray diffraction at the plural points appearing in the neighborhood of the intersection points between the Debye-ring of the X-ray diffraction and the equatorial line when the number of plots is increased.

In the stress analysis based on the $2\theta$-$\sin^2 \Psi$ method, the measurement result is higher in precision as the amount of X-ray diffraction information plotted on the $2\theta$-$\sin^2 \Psi$ is larger. Therefore, as indicated by filled circles and filled diamonds in FIG. 9, attention is focused on X-ray diffractions at plural points appearing in the neighborhood of the intersecting point between the Debye-ring of each X-ray diffraction and the equatorial line. The diffraction angles $2\theta$ determined from the X-ray diffractions at the plural points and the $\sin^2 \Psi$ values to which the $\Psi$ angles are converted are plotted on the $2\theta$-$\sin^2 \Psi$ diagram as shown in FIG. 10. The X-ray diffractions at the plural points appearing in the neighborhood of the intersection point between the Debye-ring and the equatorial line can be regarded as X-ray diffractions at different $\Psi$ angles as described with reference to FIGS. 3A and 3B.

As described above, a $2\theta$-$\sin^2 \Psi$ line can be determined by linearly approximating the points plotted on the $2\theta$-$\sin^2 \Psi$ diagram with respect to the plural $\Psi$ angles as shown in FIG. 10. The gradient of this $2\theta$-$\sin^2 \Psi$ line is calculated by using the least square method, and the thus-calculated gradient is multiplied by a X-ray stress constant K to obtain the stress value of the sample 1 as a measurement target. The X-ray stress constant K is a constant determined by the material of the sample 1 and the wavelength of the X-ray applied for the measurement.

[Example of Measurement of Stress Gradient in Depth Direction]

Next, an example for stress gradient measurement in the depth direction of a sample based on the X-ray stress measurement method according to the present invention will be described with reference to FIGS. 11 to 18.

In this example, the stress of the sample 1 is determined according to the $2\theta$-$\sin^2 \Psi$ method described above by using the two X-ray sources 21 and 22 for emitting X-rays having different wavelengths to analyze the stress gradient in the depth direction of the sample 1.

Specifically, X-ray sources 21 and 22 for emitting X-rays of K$\alpha$ (Cr—K$\alpha$) radiated from a Cr target and X-ray sources 21 and 22 for emitting X-rays of K$\alpha$ (Co—K$\alpha$) radiated from a Co target are used, and the offset angle of the respective X-ray sources 21 and 22 is set to 25° (that is, the X-ray sources are arranged at an angular interval of 25°), and the sample 1 is irradiated with X-rays at different incident angles from the respective X-ray sources 21 and 22.

Figure 11:
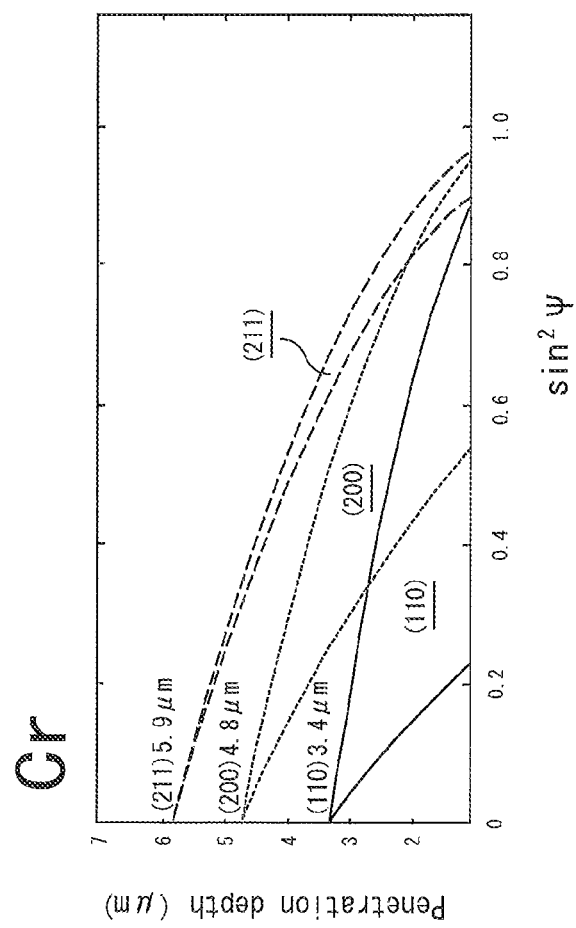
FIG. 11 is a diagram showing a penetration depth range of X-ray when X-ray having the wavelength of Cr—K$\alpha$ is incident to $\alpha$-Fe, wherein the ordinate axis represents the penetration depth of X-ray and the abscissa axis represents $\sin^2\theta$ (corresponding to the incident angle of the X-ray)
Figure 12:
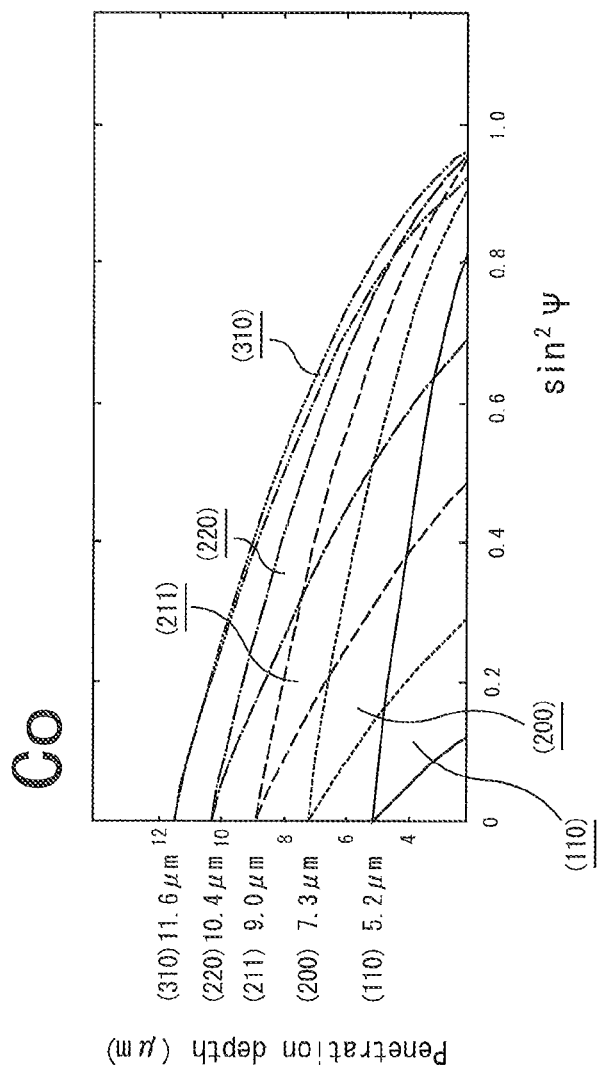
FIG. 12 is a diagram showing a penetration depth range of X-ray when X-ray having the wavelength of Co—K$\alpha$ is incident to $\alpha$-Fe, wherein the ordinate axis represents the penetration depth of X-ray and the abscissa axis represents $\sin^2\theta$ (corresponding to the incident angle of the X-ray)

FIG. 11 is a diagram showing the penetration depth range when the X-ray having the wavelength of Cr—K$\alpha$ is incident to $\alpha$-Fe, wherein the ordinate axis represents the penetration depth of X-ray and the abscissa axis represents $\sin^2 \Psi$ (corresponding to the incident angle of the X-ray). FIG. 12 is a diagram showing a penetration depth range when X-ray having the wavelength of Co—K$\alpha$ is incident to $\alpha$-Fe, wherein the ordinate axis represents the penetration depth of X-ray and the abscissa axis represents $\sin^2 \Psi$ (corresponding to the incident angle of the X-ray).

As is apparent from these diagrams, the penetration depth of X-ray to the sample 1 is determined by the lattice plane from which the X-ray is diffracted, the wavelength of the incident X-ray and the incident angle $\Psi_0$ (in FIG. 12, the incident angle $\Psi_0$ is converted to $\sin^2 \Psi$ and displayed). Therefore, the lattice plane from which the information of X-ray diffraction from a target depth point of the sample 1 is obtained, the wavelength of the incident X-ray and the incident angle $\Psi_0$ ($\sin^2 \Psi$) of the X-ray are determined by referring to FIGS. 11 and 12.

Figure 13:
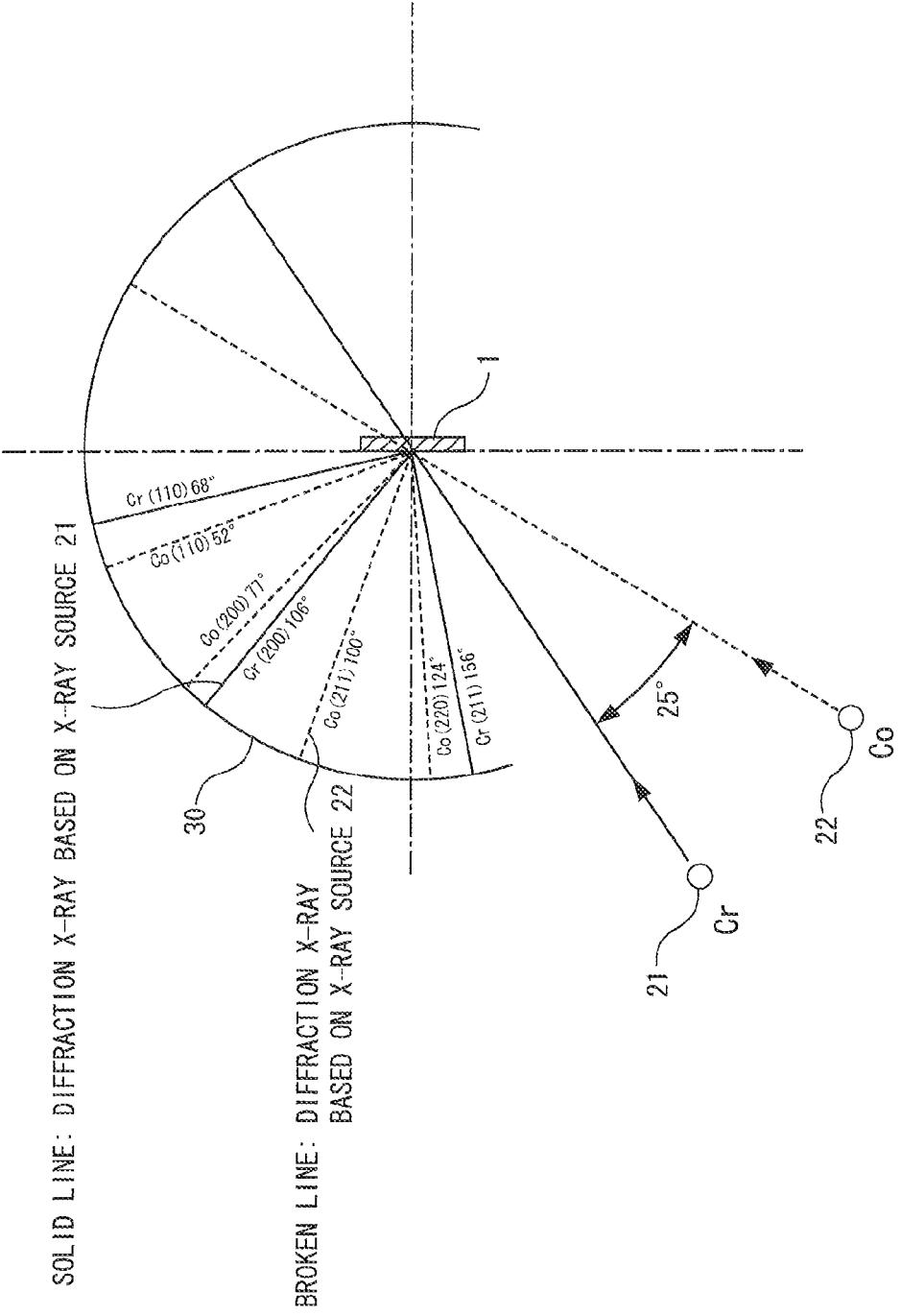
FIG. 13 is a diagram showing an example relating to stress gradient measurement in the depth direction of the sample based on the X-ray stress measurement method according to the present invention.

Next, when the sample 1 is irradiated with X-ray from each of the X-ray sources 21 and 22 at the determined incident angle $\Psi_0$ of X-ray, X-ray diffractions diffracted from the lattice planes in the sample 1 are recorded on the image plate 30 as shown in FIG. 13.

Figure 14:
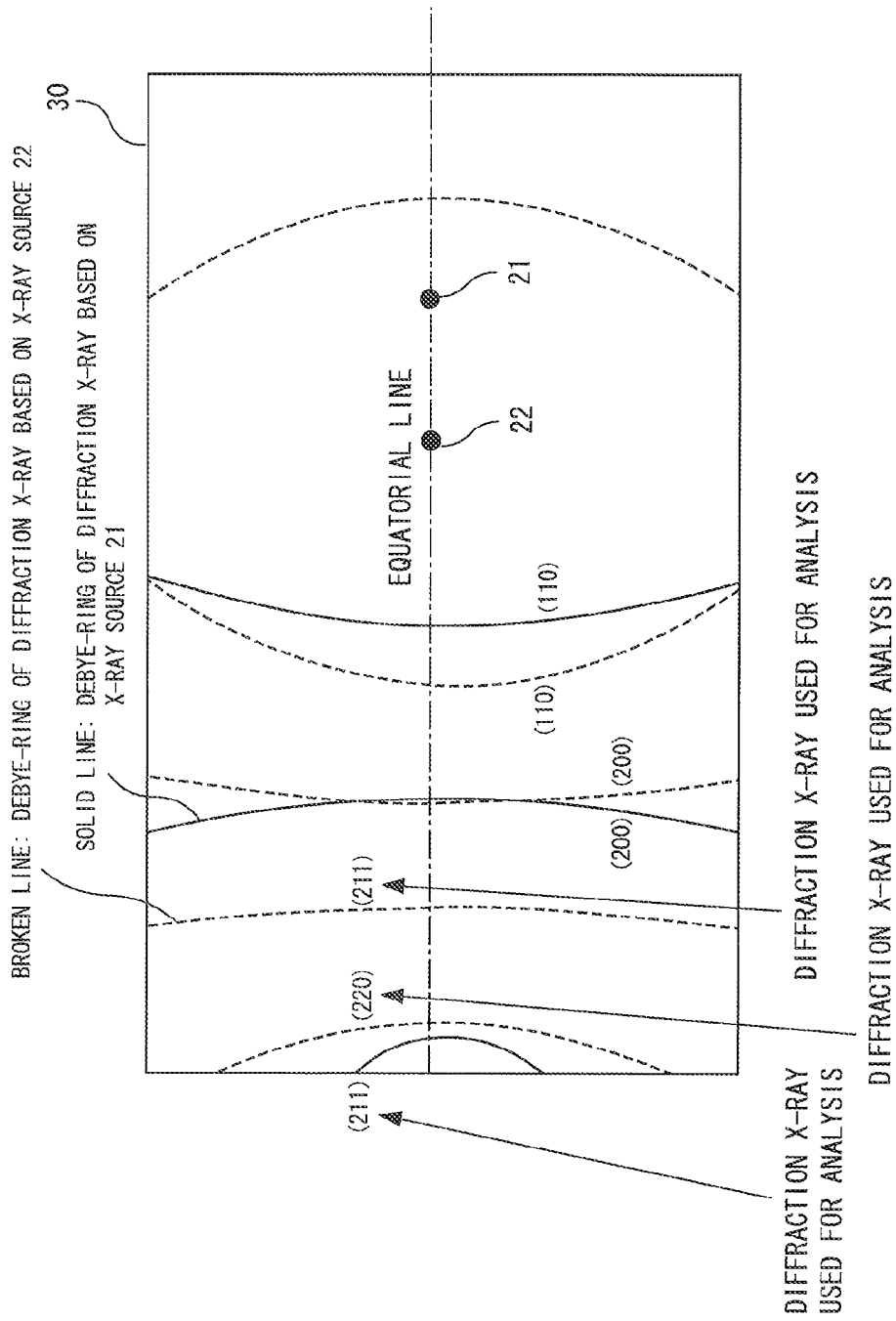
FIG. 14 is a diagram showing information of X-ray diffraction recorded on the image plate in the stress gradient measurement in the depth direction of the sample based on the X-ray stress measurement method according to the present invention.

In this example, as shown in FIG. 14, the stress of the sample 1 is determined according to the $2\theta$-$\sin^2 \Psi$ method by using the information of the X-ray diffraction diffracted from the (211) lattice plane with respect to the incident X-ray of Cr—K$\alpha$, the information of the X-ray diffraction diffracted from the (211) lattice plane with respect to the incident X-ray of Co—K$\alpha$ and the information of the X-ray diffraction diffracted from the (220) lattice plane with respect to the incident X-ray of Co—K$\alpha$ out of X-ray diffractions recorded on the image plate 30.

FIGS. 15A to 15D are $2\theta$-$\sin^2 \Psi$ diagrams obtained on the basis of the information of the X-ray diffraction diffracted from the (211) lattice plane with respect to the incident X-ray of Cr—K$\alpha$.

Figure 15B:
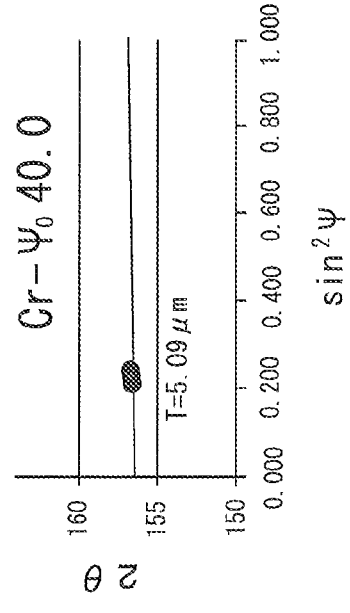
FIGS. 15A to 15D are diagrams showing $2\theta$-$\sin^2\Psi$ lines determined on the basis of information of X-ray diffracted from $\alpha$-Fe (211) plane in association with incident X-ray of Cr—K$\alpha$.
Figure 15A:
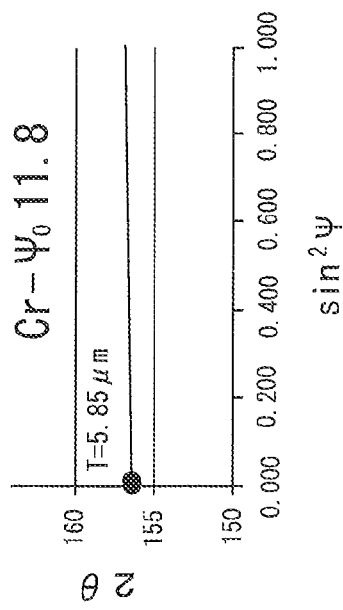

FIG. 15A is the $2\theta$-$\sin^2 \Psi$ diagram obtained by plotting $2\theta$ obtained from the X-ray diffraction on the equatorial line recorded on the image plate 30 and the value of $\sin^2 \Psi$ to which the $\Psi$ angle is converted when X-ray is incident at the incident angle $\Psi_0$=11.8°. When X-ray is incident to the (211) lattice plane at the incident angle $\Psi_0$=11.8°, the $\Psi$ angle is equal to 0°. Therefore, only one point is plotted in FIG. 15A.

When X-ray of Cr—K$\alpha$ is incident to the sample 1 of $\alpha$-Fe at the incident angle $\Psi_0$=11.8°, X-ray diffraction appears from the (211) lattice plane in the neighborhood of 5.85 $\mu$m in depth.

FIG. 15B is the $2\theta$-$\sin^2 \Psi$ diagram obtained by plotting $2\theta$ obtained from the X-ray diffraction on the equatorial line recorded on the image plate 30 and the value of $\sin^2 \Psi$ to which the $\Psi$ angle is converted when X-ray is incident at the incident angle $\Psi_0$=40.0°. In FIG. 15B, in addition to the X-ray diffraction on the equatorial line recorded on the image plate 30, attention is focused on X-ray diffractions at plural points appearing in the neighborhood of the intersection point between the Debye-ring of the X-ray diffraction and the equatorial line (that is, X-ray diffractions at plural points other than the intersecting points between the Debye-ring of the X-ray diffraction and the equatorial line), and the diffraction angles $2\theta$ determined from the information of the respective X-ray diffractions and the values of $\sin^2 \Psi$ to which the $\Psi$ angles are converted are plotted at the plural points on the $2\theta$-$\sin^2 \Psi$ diagram.

When X-ray of Cr—K$\alpha$ is incident to the sample 1 of $\alpha$-Fe at the incident angle $\Psi_0$=40.0°, X-ray diffraction appears from the (211) lattice plane in the neighborhood of 5.09 μm in depth.

Figure 15D:
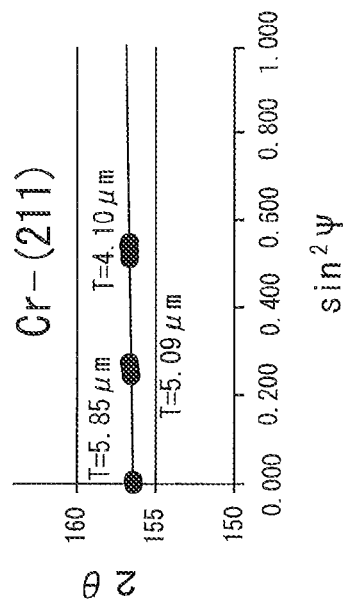
Figure 15C:
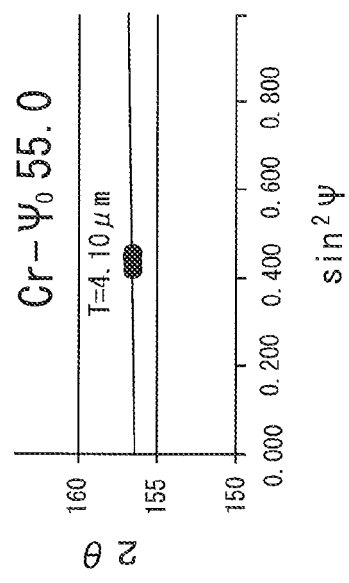

FIG. 15C is the $2\theta$-$\sin^2 \Psi$ diagram obtained by plotting $2\theta$ obtained from the X-ray diffraction on the equatorial line recorded on the image plate 30 and the value of $\sin^2 \Psi$ to which the $\Psi$ angle is converted when X-ray is incident at the incident angle $\Psi_0$=55.0°. In FIG. 15C, in addition to the X-ray diffraction on the equatorial line recorded on the image plate 30, attention is focused on X-ray diffractions at plural points appearing in the neighborhood of the intersection point between the Debye-ring of the X-ray diffraction and the equatorial line (that is, X-ray diffractions at plural points other than the intersecting points between the Debye-ring of the X-ray diffraction and the equatorial line), and the diffraction angles $2\theta$ determined from the information of the respective X-ray diffractions and the values of $\sin^2 \Psi$ to which the $\Psi$ angles are converted are plotted at the plural points on the $2\theta$-$\sin^2 \Psi$ diagram.

When X-ray of Cr—K$\alpha$ is incident to the sample 1 of $\alpha$-Fe at the incident angle $\Psi_0$=55.0°, X-ray diffraction appears from the (211) lattice plane in the neighborhood of 4.10 μm in depth.

FIG. 15D is the diagram in which all the plotted points in the $2\theta$-$\sin^2 \Psi$ diagrams of FIGS. 15A, 15B and 15C are collectively shown. The $2\theta$-$\sin^2 \Psi$ line is obtained by linearly approximating the plotted points in the $2\theta$-$\sin^2 \Psi$ diagram of FIG. 15D. Furthermore, the gradient is calculated by using the least square method with respect to the $2\theta$-$\sin^2 \Psi$ line, and the calculated gradient is multiplied by the X-ray stress constant K, thereby determining the target stress value of the sample 1. The X-ray stress constant K is a constant determined by the material of the sample 1 and the wavelength of the X-ray used for the measurement as described above.

The thus-obtained stress represents stress in the neighborhood of the X-ray penetration depth from 4.10 μm to 5.85 μm.

Next, FIGS. 16A to 16D are $2\theta$-$\sin^2 \Psi$ diagrams obtained on the basis of the information of the X-ray diffraction diffracted from the (211) lattice plane with respect to the incident X-ray of Co—K$\alpha$.

FIG. 16A is the $2\theta$-$\sin^2 \Psi$ diagram which is plotted on the basis of the information of the X-ray diffraction recorded on the image plate 30 when X-ray is irradiated at the incident angle $\Psi_0$=36.8°. When X-ray of Co—K$\alpha$ is incident to the sample 1 of $\alpha$-Fe at the incident angle $\Psi_0$=36.8°, X-ray diffraction appears from the (211) lattice plane in the neighborhood of 9.02 μm in depth.

FIG. 16B is the $2\theta$-$\sin^2 \Psi$ diagram which is plotted on the basis of the information of the X-ray diffraction recorded on the image plate 30 when X-ray is irradiated at the incident angle $\Psi_0$=65.0°. When X-ray of Co—K$\alpha$ is incident to the sample 1 of $\alpha$-Fe at the incident angle $\Psi_0$=65.0°, X-ray diffraction appears from the (211) lattice plane in the neighborhood of 6.96 μm in depth.

FIG. 16C is the $2\theta$-$\sin^2 \Psi$ diagram which is plotted on the basis of the information of the X-ray diffraction recorded on the image plate 30 when X-ray is irradiated at the incident angle $\Psi_0$=80.0°. When X-ray of Co—K$\alpha$ is incident to the sample 1 of $\alpha$-Fe at the incident angle $\Psi_0$=80.0°, X-ray diffraction appears from the (211) lattice plane in the neighborhood of 3.50 μm in depth.

FIG. 16D is the diagram in which all the plotted points in the $2\theta$-$\sin^2 \Psi$ diagrams of FIGS. 16A, 16B and 16C are collectively shown. The $2\theta$-$\sin^2 \Psi$ line is obtained by linearly approximating the plotted points in the $2\theta$-$\sin^2 \Psi$ diagram of FIG. 16D. Furthermore, the gradient is calculated by using the least square method with respect to the $2\theta$-$\sin^2 \Psi$ line, and the calculated gradient is multiplied by the X-ray stress constant K, thereby determining the target stress value of the sample 1. The X-ray stress constant K is a constant determined by the material of the sample 1 and the wavelength of the X-ray used for the measurement as described above.

The thus-obtained stress represents stress in the neighborhood of the X-ray penetration depth from 3.50 μm to 9.02 μm.

FIGS. 17A to 17D are $2\theta$-$\sin^2 \Psi$ diagrams obtained on the basis of the information of the X-ray diffraction diffracted from the (200) lattice plane with respect to the incident X-ray of Co—K$\alpha$.

Figure 17B:
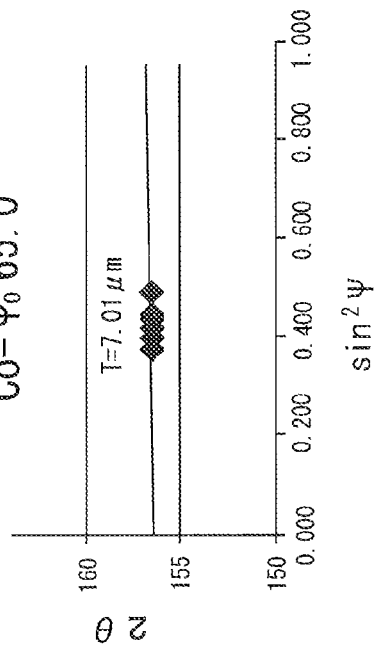
FIGS. 17A to 17D are diagrams showing $2\theta$-$\sin^2 \Psi$ lines determined on the basis of information of X-ray diffracted from $\alpha$-Fe (200) plane in association with incident X-ray of Co—K$\alpha$.
Figure 17D:
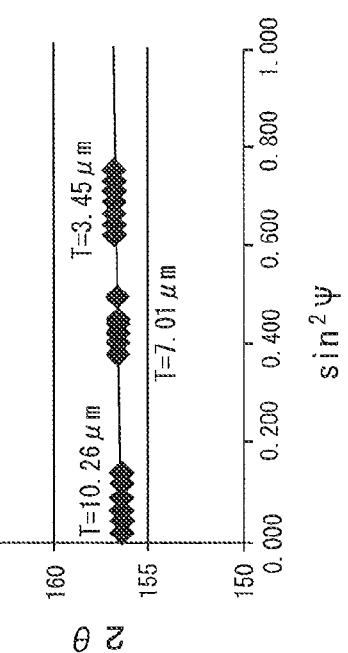
Figure 17A:
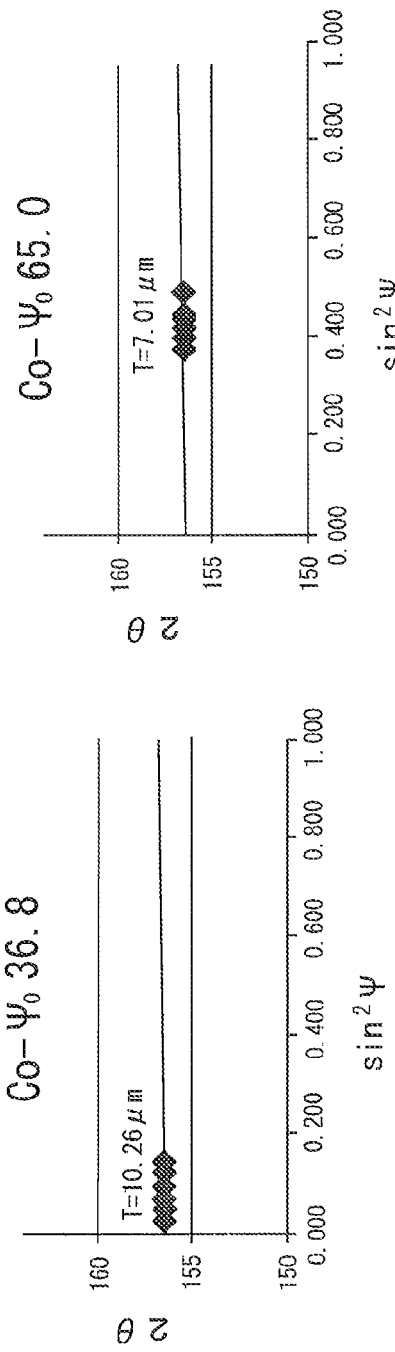

FIG. 17A is the $2\theta$-$\sin^2 \Psi$ diagram which is plotted on the basis of the information of the X-ray diffraction recorded on the image plate 30 when X-ray is irradiated at the incident angle $\Psi_0$=36.8°. When X-ray of Co—K$\alpha$ is incident to the sample 1 of $\alpha$-Fe at the incident angle $\Psi_0$=36.8°, X-ray diffraction appears from the (200) lattice plane in the neighborhood of 10.26 μm in depth.

FIG. 17B is the $2\theta$-$\sin^2 \Psi$ diagram which is plotted on the basis of the information of the X-ray diffraction recorded on the image plate 30 when X-ray is irradiated at the incident angle $\Psi_0$=65.0°. When X-ray of Co—K$\alpha$ is incident to the sample 1 of $\alpha$-Fe at the incident angle $\Psi_0$=65.0°, X-ray diffraction appears from the (200) lattice plane in the neighborhood of 7.01 μm in depth.

Figure 17C:
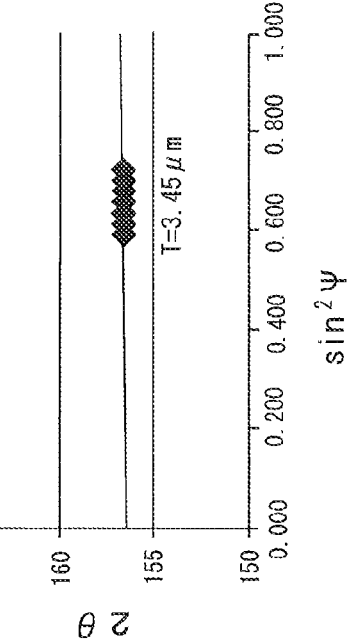

FIG. 17C is the $2\theta$-$\sin^2 \Psi$ diagram which is plotted on the basis of the information of the X-ray diffraction recorded on the image plate 30 when X-ray is irradiated at the incident angle $\Psi_0$=80.0°. When X-ray of Co—K$\alpha$ is incident to the sample 1 of $\alpha$-Fe at the incident angle $\Psi_0$=80.0°, X-ray diffraction appears from the (200) lattice plane in the neighborhood of 3.45 μm in depth.

FIG. 17D is the diagram in which all the plotted points in the $2\theta$-$\sin^2 \Psi$ diagrams of FIGS. 17A, 17B and 17C are collectively shown. The $2\theta$-$\sin^2 \Psi$ line is obtained by linearly approximating the plotted points in the $2\theta$-$\sin^2 \Psi$ diagram of FIG. 17D. Furthermore, the gradient is calculated by using the least square method with respect to the $2\theta$-$\sin^2 \Psi$ line, and the calculated gradient is multiplied by the X-ray stress constant K, thereby determining the target stress value of the sample 1. The X-ray stress constant K is a constant determined by the material of the sample 1 and the wavelength of the X-ray used for the measurement as described above.

The thus-obtained stress represents stress in the neighborhood of the X-ray penetration depth of 3.45 μm to 10.26 μm.

Figure 18:
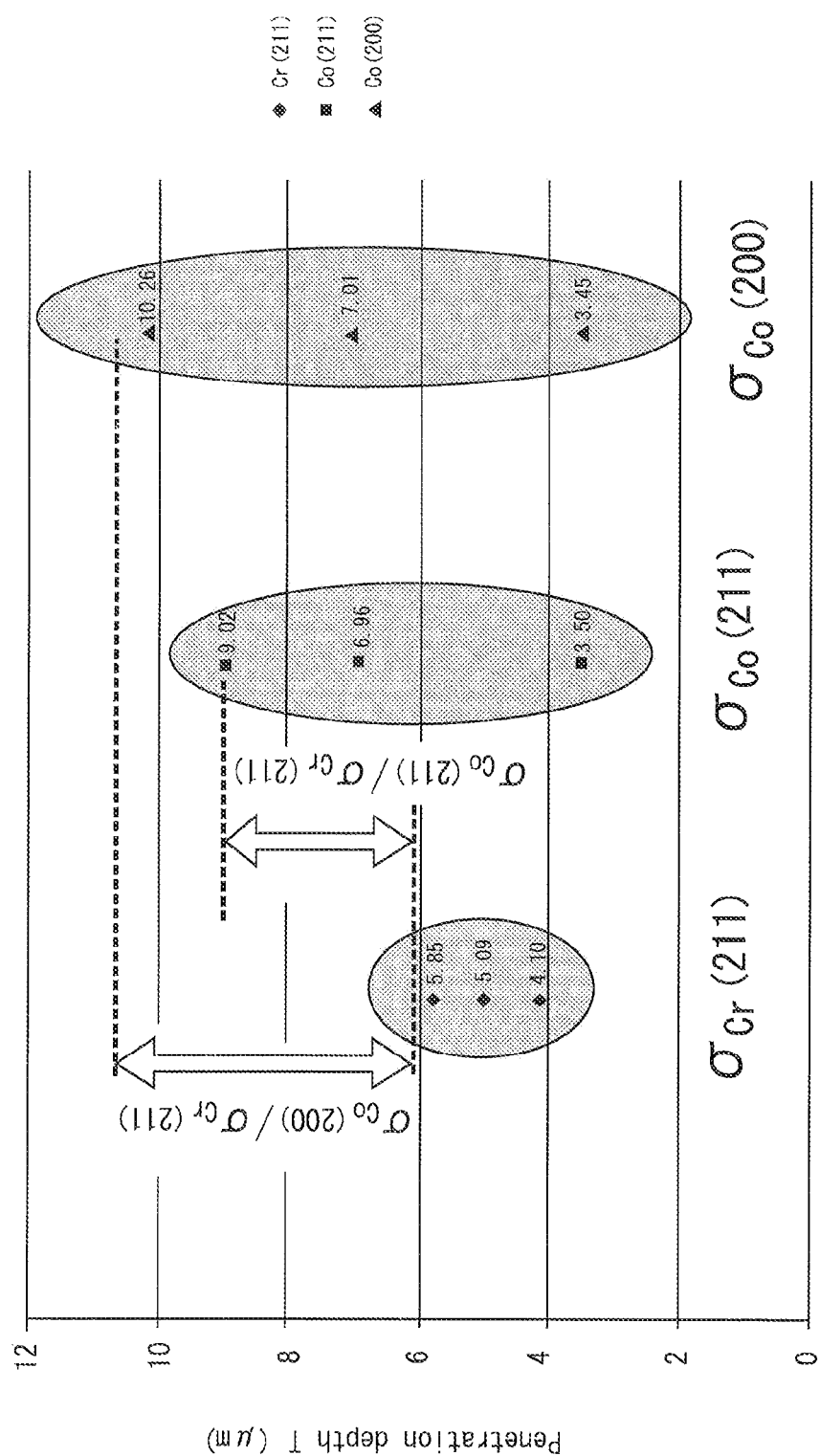
FIG. 18 is a diagram showing a stress depth range determined by the stress gradient measurement in the depth direction of the sample based on the X-ray stress measurement method according to the present invention.

FIG. 18 is a diagram showing the depth range of the stress determined as described above. The stress gradients $\sigma_{Co}$ (211)/$\sigma_{Cr}$ (211) and $\sigma_{Co}$ (200)/$\sigma_{Cr}$ (211) in the depth direction of the sample 1 can be calculated from the stresses in the respective depth ranges $\sigma_{Cr}$ (211), $\sigma_{Co}$ (211) and $\sigma_{Co}$ (200).

[Measurement of Distribution in Depth Direction of Retained Austenite]

Next, a measurement of the distribution in the depth direction of retained austenite according to the X-ray stress measurement method of the present invention will be described.

Texture of austenite (Y-Fe) may remain in quenched steel material or stainless material.

Here, it is well known from the Bragg equation that the diffraction angle $2\theta$ of X-ray is determined on the basis of the wavelength of incident X-ray and the interval of lattice planes from which the X-ray is diffracted. For example, when austenite (Y-Fe) is irradiated with X-ray of Cr—K$\alpha$, the diffraction angle $2\theta$ of X-ray diffraction diffracted from (200) lattice planes is equal to about 79°. Likewise, when austenite (γ-Fe) is irradiated with X-ray of Co—Kα, the diffraction angle 2θ of X-ray diffraction diffracted from (200) lattice planes is equal to about 60°. Furthermore, as described above, the penetration depth of incident x-ray is determined on the basis of the wavelength of the incident X-ray, the incident angle and the lattice planes from which the X-ray is diffracted as described above.

Accordingly, the wavelengths of X-rays (incident X-rays) emitted from the two X-ray sources 21 and 22 and the incident angles of the emitted X-rays to the sample 1 are set, the sample 1 is irradiated with X-rays from the respective X-ray sources 21 and 22, and the information of X-ray diffractions diffracted from the lattice planes in the sample 1 is collectively recorded on the image plate 30.

Subsequently, it is determined on the basis of the information (diffraction angle 2θ) of each of the X-ray diffractions recorded on the image plate 30 whether the X-ray diffraction is diffracted from the lattice planes of austenite, whereby existence of retained austenite can be checked. Furthermore, since the penetration depth of incident X-ray is determined on the basis of the wavelength of the incident X-ray, the incident angle and the lattice planes from which the X-ray is diffracted, the distribution condition in the depth direction of retained austenite can be grasped from the information of the X-ray diffractions.

In this embodiment, the sample 1 is irradiated with X-rays having different wavelength at different incident angles from the two X-ray sources 21 and 22, whereby the information of X-ray diffractions from different depths can be obtained in a lump. Therefore, the measurement frequency (frequency of scanning) required to obtain information necessary for determining the distribution condition in the depth direction of retained austenite in the sample 1 can be remarkably reduced, and the rapid measurement can be performed.

The present invention is not limited to the above embodiment and the above examples, and various modifications and applications may be made without departing from the subject matter of the present invention. For example, in the above embodiment and the examples, two X-ray sources are used. However, three or more X-ray sources may be used according to the need.

The invention claimed is:

1. An X-ray stress measurement method comprising:
    irradiating a sample with X-rays at a plurality of different incident angles from a plurality of X-ray sources;
    focusing attention on a Debye-ring of each X-ray diffraction radiated conically from the sample in association with incident X-ray emitted from each of the X-ray sources; and
    determining stress in the sample on the basis of information of X-ray diffraction appearing at an intersection point between the Debye-ring and an equatorial plane containing an optical axis of the incident X-ray emitted from each of the X-ray sources, and information of X-ray diffraction appearing at a point on the Debye-ring other than the intersection point between the Debye-ring and the equatorial plane.

2. The X-ray stress measurement method according to claim 1, wherein X-rays having different wavelengths are emitted from the plurality of X-ray sources to determine a stress gradient in a depth direction of the sample.

3. The X-ray stress measurement method according to claim 2, wherein stress at a desired depth is determined by specifying the wavelengths of the X-rays emitted from the plurality of X-ray sources and setting the incident angles of the X-rays to the sample, and the stress gradient in the depth direction of the sample is determined on the basis of a measurement result of stress at different depths.

4. The X-ray stress measurement method according to claim 1, wherein the sample is formed of steel material, and a distribution in the depth direction of retained austenite in the sample is determined.

5. The X-ray stress measurement method according to claim 1, wherein the stress of the sample is determined by changing a relative intersection angle between the optical axes of the X-rays emitted from the plurality of X-ray sources.

6. The X-ray stress measurement method according to claim 5, wherein the stress of the sample is determined according to a $2\theta\text{-sin}^2\Psi$ method by changing the incident angles of the X-rays with which the sample is irradiated from the plurality of X-ray sources.

7. An X-ray stress measurement apparatus comprising:
    a sample table on which a sample is mounted;
    a plurality of X-ray sources that irradiate the sample with X-rays;
    an X-ray detector that detects X-ray diffractions diffracted from crystal lattice planes in the sample;
    an apparatus main body in which the sample table, the X-ray sources and the X-ray detector are mounted; and
    an analyzer that determines stress in the sample on the basis of information of the X-ray diffractions detected by the X-ray detector, wherein the plurality of X-ray sources are arranged so as to make X-rays incident to a desired incident point set on a surface of the sample at different incident angles, the X-ray detector has a function capable of collectively detecting plural X-ray diffractions emitted from the sample, and the analyzer focuses attention to a Debye-ring of X-ray diffraction radiated conically from the sample in association with incident X-ray emitted from each of the X-ray sources, and determines stress in the sample on the basis of information of X-ray diffraction appearing at an intersection point between the Debye-ring and an equatorial plane containing the optical axis of the incident X-ray emitted from each of the X-ray sources, and information of X-ray diffraction appearing at a point on the Debye-ring other than the intersection point between the Debye-ring and the equatorial plane.

8. The X-ray stress measurement apparatus according to claim 7, wherein the plurality of X-ray sources are configured to emit X-rays having different wavelengths, and the analyzer has a function of determining a stress gradient in a depth direction of the sample.

9. The X-ray stress measurement apparatus according to claim 8, wherein the sample is formed of steel material and the analyzer has a function of determining a distribution of retained austenite in the depth direction of the sample.

10. The X-ray stress measurement apparatus according to claim 7, further comprising an angle adjusting unit that changes a relative intersection angle between optical axes of the respective X-rays emitted from the plurality of X-ray sources.

11. The X-ray stress measurement apparatus according to claim 10, further comprising an incident angle changing mechanism that rotates the sample table around an axis that passes through the incident point and is perpendicular to the equatorial plane to change the incident angles of the respective X-rays emitted from the plurality of X-ray sources to the sample, wherein the plurality of X-ray sources are mounted in the apparatus main body, and the analyzer has a function of determining stress of the sample according to a $2\theta\text{-sin}^2\Psi$ method.

12. The X-ray stress measurement apparatus according to claim 11, wherein the X-ray detector comprises an image plate, and is disposed arcuately around the sample so as to be capable of capturing X-ray diffractions emitted from the sample.

* * * * *